(12) United States Patent
Reifman et al.

(10) Patent No.: US 11,241,194 B2
(45) Date of Patent: Feb. 8, 2022

(54) METHOD AND SYSTEM FOR MEASURING, PREDICTING, AND OPTIMIZING HUMAN COGNITIVE PERFORMANCE

(71) Applicant: The Government of the United States, as represented by the Secretary of the Army, Ft. Detrick, MD (US)

(72) Inventors: Jaques Reifman, New Market, MD (US); Jianbo Liu, Lexington, VA (US); Nancy Wesensten, Silver Spring, MD (US); Thomas Balkin, Ellicott City, MD (US); Sridhar Ramakrishnan, Frederick, MD (US); Maxim Y. Khitrov, Rockville, MD (US)

(73) Assignee: The Government of the United States, as represented by the Secretary of the Army, Fort Detrick, MD (US)

( * ) Notice: Subject to any disclaimer, the term of this patent is extended or adjusted under 35 U.S.C. 154(b) by 760 days.

(21) Appl. No.: 15/580,907

(22) PCT Filed: Jun. 8, 2016

(86) PCT No.: PCT/US2016/036532
§ 371 (c)(1),
(2) Date: Dec. 8, 2017

(87) PCT Pub. No.: WO2016/201008
PCT Pub. Date: Dec. 15, 2016

(65) Prior Publication Data
US 2018/0289314 A1 Oct. 11, 2018

Related U.S. Application Data

(60) Provisional application No. 62/172,347, filed on Jun. 8, 2015.

(51) Int. Cl.
*A61B 5/00* (2006.01)
*A61B 5/16* (2006.01)
(Continued)

(52) U.S. Cl.
CPC .............. *A61B 5/486* (2013.01); *A61B 5/00* (2013.01); *A61B 5/02* (2013.01); *A61B 5/0255* (2013.01);
(Continued)

(58) Field of Classification Search
None
See application file for complete search history.

(56) References Cited

U.S. PATENT DOCUMENTS

| 4,770,636 A | 9/1988 | Buschke |
| 4,893,291 A | 1/1990 | Bick et al. |

(Continued)

FOREIGN PATENT DOCUMENTS

| WO | WO 88/10091 A1 | 12/1988 |
| WO | WO 89/02098 A1 | 3/1989 |

(Continued)

OTHER PUBLICATIONS

Redmond et al., "Observations on the Design and Specifications of a Wrist-Worn Human Activity Monitoring System," Behavior Research Methods, Instruments, & Computers, 1985, pp. 659-669, vol. 17, Issue 6.

(Continued)

*Primary Examiner* — Michael R Bloch
(74) *Attorney, Agent, or Firm* — Leigh Callander

(57) ABSTRACT

A system, method and apparatus is disclosed, comprising a biomathetical model for optimizing cognitive performance in the face of sleep deprivation that integrates novel and nonobvious biomathematical models for quantifying performance impairment for both chronic sleep restriction and
(Continued)

total sleep deprivation; the dose-dependent effects of caffeine on human vigilance; and the pheonotypical response of a particular user to caffeine dosing, chronic sleep restriction and total sleep deprivation in user-friendly software application which itself may be part of a networked system.

17 Claims, 17 Drawing Sheets

(51) Int. Cl.
| | |
|---|---|
| A61B 5/11 | (2006.01) |
| A61B 5/02 | (2006.01) |
| A61B 5/0255 | (2006.01) |
| A61B 5/113 | (2006.01) |
| A61B 5/103 | (2006.01) |
| G16H 15/00 | (2018.01) |
| A61B 5/18 | (2006.01) |

(52) U.S. Cl.
CPC ............. *A61B 5/103* (2013.01); *A61B 5/11* (2013.01); *A61B 5/113* (2013.01); *A61B 5/1118* (2013.01); *A61B 5/162* (2013.01); *A61B 5/165* (2013.01); *A61B 5/4806* (2013.01); *A61B 5/4839* (2013.01); *A61B 5/4857* (2013.01); *A61B 5/6898* (2013.01); *A61B 5/7225* (2013.01); *A61B 5/7275* (2013.01); *A61B 5/7435* (2013.01); *A61B 5/7475* (2013.01); *G16H 15/00* (2018.01); *A61B 5/18* (2013.01); *A61B 2503/20* (2013.01); *A61B 2560/0475* (2013.01)

(56) References Cited

U.S. PATENT DOCUMENTS

| | | | |
|---|---|---|---|
| 5,006,985 A | 4/1991 | Ehret et al. | |
| 5,197,489 A | 3/1993 | Conlan | |
| 5,230,346 A | 7/1993 | Leuchter | |
| 5,230,629 A | 7/1993 | Buschke | |
| 5,259,390 A | 11/1993 | MacLean | |
| 5,304,212 A | 4/1994 | Czeisler et al. | |
| 5,320,109 A | 6/1994 | Chamoun | |
| 5,348,370 A | 9/1994 | Fukuoka | |
| 5,433,223 A | 7/1995 | Moore-Ede et al. | |
| 5,566,067 A | 10/1996 | Hobson et al. | |
| 5,568,127 A | 10/1996 | Bang | |
| 5,570,698 A | 11/1996 | Liang et al. | |
| 5,573,013 A | 11/1996 | Conlan | |
| 5,585,785 A | 12/1996 | Gwin et al. | |
| 5,595,488 A | 1/1997 | Gozlan et al. | |
| 5,647,633 A | 7/1997 | Fukuoka | |
| 5,682,144 A | 10/1997 | Mannik | |
| 5,682,882 A | 11/1997 | Lieberman | |
| 5,689,241 A | 11/1997 | Clarke, Sr. et al. | |
| 5,691,693 A | 11/1997 | Kithil | |
| 5,720,294 A | 2/1998 | Skinner | |
| 5,762,072 A | 6/1998 | Conlan et al. | |
| 5,813,993 A | 9/1998 | Kaplan et al. | |
| 5,911,581 A | 6/1999 | Reynolds et al. | |
| 5,995,868 A | 11/1999 | Dorfmeister et al. | |
| 6,066,092 A | 5/2000 | Cady et al. | |
| 6,070,098 A | 5/2000 | Moore-Ede et al. | |
| 6,113,538 A | 9/2000 | Bowles et al. | |
| 6,241,686 B1 | 6/2001 | Balkin et al. | |
| 6,287,262 B1* | 9/2001 | Amano ............. A61B 5/02055 600/500 |
| 6,419,629 B1 | 7/2002 | Balkin et al. | |
| 6,527,715 B2 | 3/2003 | Balkin et al. | |
| 6,530,884 B2 | 3/2003 | Balkin et al. | |
| 6,553,252 B2 | 4/2003 | Balkin et al. | |
| 6,579,233 B2 | 6/2003 | Hursh | |
| 6,740,032 B2 | 5/2004 | Balkin et al. | |
| 6,743,167 B2 | 6/2004 | Balkin et al. | |
| 7,118,530 B2 | 10/2006 | Hursh et al. | |
| 7,621,871 B2 | 11/2009 | Downs, III et al. | |
| 7,766,827 B2 | 8/2010 | Balkin et al. | |
| 8,273,035 B2 | 9/2012 | Russo et al. | |
| 8,285,375 B2 | 10/2012 | Sing | |
| 8,712,827 B2 | 4/2014 | Mollicone et al. | |
| 8,781,796 B2 | 7/2014 | Mott et al. | |
| 2001/0056225 A1 | 12/2001 | DeVito | |
| 2002/0183644 A1 | 12/2002 | Levendowski et al. | |
| 2003/0018242 A1 | 1/2003 | Hursh et al. | |
| 2004/0049132 A1* | 3/2004 | Barron ............. A61B 5/113 600/595 |
| 2005/0033122 A1* | 2/2005 | Balkin .............. G16H 50/50 600/300 |
| 2005/0177031 A1 | 8/2005 | Hursh | |
| 2006/0202037 A1 | 9/2006 | Gunawardena et al. | |
| 2008/0294019 A1* | 11/2008 | Tran ............. A61B 5/04005 600/301 |
| 2009/0048540 A1* | 2/2009 | Otto ............. A61B 5/6831 600/595 |
| 2012/0191425 A1* | 7/2012 | Mott ............. A61B 5/16 703/2 |
| 2013/0018284 A1* | 1/2013 | Kahn ............. A61B 5/681 600/595 |
| 2013/0072823 A1* | 3/2013 | Kahn ............. A61B 5/4806 600/595 |
| 2014/0149063 A1 | 5/2014 | Reifman et al. | |
| 2015/0104771 A1* | 4/2015 | Bernstein ............. A61B 5/165 434/236 |

FOREIGN PATENT DOCUMENTS

| | | |
|---|---|---|
| WO | WO 90/00777 A1 | 1/1990 |
| WO | WO 00/26840 A1 | 5/2000 |
| WO | WO 02/26841 A1 | 5/2000 |
| WO | WO 02/073342 A1 | 9/2002 |
| WO | WO 02/073343 A2 | 9/2002 |
| WO | 2015054134 A1 | 4/2015 |

OTHER PUBLICATIONS

Rosekind et al., "Alertness Management in Long-Haul Flight Operations," Proceedings of the 39.sup.th Annual Corporate Aviation Safety Seminar, 1994, pp. 167-178 (printed from the NASA website).

Shi et al., "Using Artificial Neural Network for Sleep/Wake Discrimination from Wrist Activity: Preliminary Results," Proceedings of the 20.sup.th Annual International Conference of the IEEE Engineering in Medicine and Biology Society, 1998, pp. 1113-1115, vol. 20, No. 3.

Sing et al., "High-Frequency EEG as Measure of Cognitive Function Capacity: A Preliminary Report," Aviation, Space and Environmental Medicine, Jul. 2005, pp. C114-C135, vol. 7, No. 7, Section II.

"Science & Technology Watch," Aviation, Space, and Environmental Medicine, Dec. 2007, p. 1178, vol. 78, No. 12.

Wesensten et al., "Reversal of Triazolam and Zolpidem-Induced Memory Impairment by Flumazenil," Psychopharmacology, 1995, Abstract, vol. 121.

Thorne et al., "Plumbing Human Performance Limits During 72 Hours of High Task Load," Proceedings of the 24th DRG Seminar on the Human as a Limiting Element in Military Systems, pp. 1-24.

Van Someren, Eus J.W., "Actigraphic Monitoring of Movement and Rest-Activity Rhythms in Aging, Alzheimer's Disease, and Parkinson's Disease," IEEE Transactions on Rehabilitation Engineering, Dec. 1997, pp. 394-398, vol. 5, No. 4.

Walsleben et al., "Sleep Habits of Long Island Rail Road Commuters," Sleep, Sep. 1999, pp. 728-734, vol. 22, No. 6.

Wesensten et al., "Performance and Alertness Effects of Caffeine, Dextroamphetamine, and Modafinil During Sleep Deprivation," Journal of Sleep Research, 2005, pp. 255-266, vol. 14.

Cambridge Neurotechnology, "The Actiwatch-Score," pre-1999.

Cambridge Neurotechnology, "The Actiwatch Software," pre-1999.

(56) References Cited

OTHER PUBLICATIONS

Cambridge Neurotechnology, "The Actiwatch and Actiwatch Plus," pre-1999.
Cambridge Neurotechnology, "Actiwatch from Cambridge Neurotechnology," printed from company website at http://www.camntech.co.uk/main.html, Sep. 18, 1998.
National Highway Traffic Safety Administration, "Drowsy Driving and Automobile Crashes", NCSDR/HTSA Expert Panel on Driver Fatigue and Sleepiness (DOT HS 808 707), Apr. 1998, pp. 1-30.
The Center for National Truck Statistics, "Truck and Bus Accident Factbook 1994," Oct. 1996, pp. 1-103.
WCBS, "Exclusive: Nuclear Plant Guards Asleep on the Job. Exelon to Terminate Deal with Security Firm also under Contract with Major Federal Agencies," WCBSTV.com, Sep. 25, 2007, printout http://wcbstv.com/politics/peach.bottom.nuclear.2.291442.html.
"AASM Publishes New Scoring Manual," Sleep Review, Apr. 18, 2007, printed from http://www.sleepreviewmag.com/sleep-report/2007-04-18-01.asp.
Akerstedt et al., "Subjective and Objective Sleepiness in the Active Individual," International Journal of Neuroscience, 1990, pp. 29-37, vol. 52.
Akerstedt et al., "The Three-Process Model of Alertness and Its Extension to Performance, Sleep Latency, and Sleep Length," Chronobiology International, 1997, pp. 115-123, vol. 14, No. 2.
Anderer et al., "An E-Health Solution for Automatic Sleep Classification According to Rechtschaffen and Kales: Validation Study of the Somnolyzer 24x7 Utilizing the Siesta Database," Neuropsychobiology, Apr. 18, 2005, pp. 115-133, vol. 51.
Angus et al., "Effects of Sleep Loss on Sustained Cognitive Performance During a Command and Control Stimulation," Behavior Research Methods, Instruments, & Computers, 1985, pp. 55-67, vol. 17, No. 1.
Balkin et al., "Comparison of the Daytime Sleep and Performance Effects of Zolpidem Versus Triazolam," Psychopharmacology, 1992, Abstract, pp. 83-88, vol. 107.
Beersma, Domien G.M , "Models of Human Sleep Regulation," Sleep Medicine Reviews, 1998, pp. 31-43, vol. 2, No. 1.
Belenky et al., "Patterns of Performance Degradation and Restoration During Sleep Restriction and Subsequent Recovery: A Sleep Dose-Response Study," European Sleep Research Society, J. Sleep Res., 2003, pp. 1-12, vol. 12.
Belenky, Gregory, "Sleep, Sleep Deprivation, and Human Performance in Continuous Operations," 1997, Walter Reed Army Institute of Research, United State Army Medical Research and Materiel Command, pp. 1-12.
Belenky et al., "Sustaining Performance During Continuous Operations: The U.S. Army's Sleep Management System," Proceedings of the Army Science Conference, 1996, pp. 1-5.
Bonnet, M.H., "Sleep Restoration as a Function of Periodic Awakening, Movement, or Electroencephalographic Change," Sleep, 1987, pp. 364-373, vol. 10, No. 4.
Boot, Max, "The New American Way of War," Foreign Affairs, Jul./Aug. 2003, available at https://www.foreignaffairs.com/articles/united-states/2003-07-01/new-american-way-war, pp. 1-13.
Braver et al., "Long Hours and Fatigue: A Survey of Tractor-Trailer Drives," Journal of Health Policy, 1992 Autumn, Abstract, vol. 13 (3).
Colburn et al., "An Ambulatory Activity Monitor with Solid State Memory," paper presented at the 13.sup.th Annual Rocky Mountain Bioengineering Symposium and 13.sup.th International ISA BioMedical Sciences Instrumentation Symposium (Instrument Society of America), May 3-5, 1976, pp. 117-122.
Coke et al., "Automatic Sleep/Wake Identification from Wrist Activity," Sleep, 1992, pp. 461-469, vol. 15, No. 5.
Dawson et al., "A Quantitative Model of Work-Related Fatigue: Background and Definition," Ergonomics, Feb. 10, 2001, pp. 144-163, vol. 44, No. 2.
Dijk et al., "Paradoxical Timing of the Circadian Rhythm of Sleep Propensity Serves to Consolidate Sleep and Wakefulness in Humans," Neuroscience Letters, pp. 63-68, vol. 166, No. 1.
Dinges et al., "Cumulative Sleepiness, Mood Disturbance, and Psychomotor Vigilance Performance Decrements During a Week of Sleep Restricted to 4-5 Hours per Night," Sleep, 1997, pp. 267-277, vol. 20, No. 4.
Dinges et al., "Principles and Guidelines for Duty and Rest Scheduling in Commercial Aviation," NASA Technical Memorandum 110404, May 1996, pp. 1-10.
Edgar et al., "Effect of SCN Lesions on Sleep in Squirrel Monkeys: Evidence for Opponent Processes in Sleep-Wake Regulation," Journal of Neuroscience, Mar. 1993, pp. 1065-1079, vol. 13, No. 3.
Fischler, Benjamin, "Review of Clinical and Psychobiological Dimensions of the Chronic Fatigue Syndrome Differentiation from Depression and Contribution of Sleep Dysfunctions," Sleep Medicine Reviews, 1999, pp. 131-146, vol. 3, No. 2.
Fletcher et al., "A Predicative Model of Work-related Fatigue Based on Hours of Work," Journal of Occupational Safety, 1997, pp. 471-485, vol. 13, No. 5.
Goldstein, Harry, "Resetting the Circadian Clock," The Pennsylvania Gazette, May 1999, available at http://www.upenn.edu/gazette/0599/goldstein.html, pp. 1-7.
Hendy et al., "Combining Time and Intensity Effects in Assessing Operator Information-Processing Load," Human Factors, 1997, pp. 30-47, vol. 39, No. 1.
Herridge, Catherine, "Pilot, 1st Officer Slept While Approaching Denver, Lawmaker Says," Fox News, Nov. 1, 2007, available at http:www.foxnews.com/story/0,2933,307019,00.html, pp. 1-3.
Hockey, G. Robert J., "Compensatory Control in the Regulation of Human Performance Under Stress and High Workload: A Cognitive-Energetical Framework," Biological Psychology, 1997, pp. 73-93, vol. 45.
Hoddes et al., "Quantification of Sleepiness: A New Approach," Pyschophysiology, Jul. 1973, pp. 431-436, vol. 10, No. 4.
Horne, James A., "Human Sleep, Sleep Loss and Behavior. Implications for the Prefrontal Cortex and Psychiatric Disorder," Br. J. Psychiatry, Mar. 1993, Abstract, pp. 413-419, vol. 162.
Horne, James A., "Sleep Loss and 'Divergent' Thinking Ability," Sleep, 1988, pp. 528-536, vol. 11, No. 6.
Johns, Murray, "Daytime Sleepiness, Snoring, and Obstructive Sleep Apnea: The Epworth Sleepiness Scale," Chest, Jan. 1993, pp. 30-36, vol. 103, No. 1.
Johns, Murray, "Rethinking the Assessment of Sleepiness," Sleep Medicine Reviews, 1998, pp. 3-15, vol. 2, No. 1.
Kaplan, R.F., "An Innovative EEG Based Approach to Drowsiness Detection," Department of Systems and Control Engineering, Case Western Reserve University, May 1996, pp. 1-242.
Knipling et al., "Crashes and Fatalities Related to Driver Drowsiness/Fatigue," U.S. Department of Transportation, Research Note, Nov. 1994, pp. 1-8.
Kripke et al., "Wrist Actigraph Measures of Sleep and Rhythms," Electoencephalography and Clinical Neurophysiology, 1978, pp. 674-676, vol. 44.
Lawlor, Maryann, "Personal Physiological Monitors Find Warfighter-Effectiveness Edge," Signal, Aug. 2000, pp. 47-50, vol. 54, No. 12.
Lubin et al., "Effects of Exercise, Bedrest and Napping on Performance Decrement During 40 Hours," Psychophysiology, pp. 334-339, Jul. 1976, vol. 13, No. 4.
Mcnally et al., SAIC Contract No. MDA903-88-D-1000: Evaluation of Sleep Discipline in Sustaining Unit Performance, Oct. 1989, pp. 1-35, Mclean, VA: Science Applications International Corporation.
Mitler et al., "Methods of Testing for Sleepiness," Behavioral Medicine, 1996, pp. 171-183, vol. 21.
Monk et al., "A Parallelism between Human Body Temperature and Performance Independent of the Endogenous Circadian Pacemaker," Journal of Biological Rhythms, Apr. 1998, pp. 113-122, vol. 13, No. 2.
Newhouse et al., "Stimulant Drug Effects on Performance and Behavior After Prolonged Sleep Deprivation: A Comparison of Amphetamine, Nicotine, and Deprenyl," Military Psychology, 1992, pp. 207-233, vol. 4.

(56) References Cited

OTHER PUBLICATIONS

Newhouse et al., "The Effects of d-Amphetamine on Arousal, Cognition, and Mood After Prolonged Total Sleep Deprivation," Neuropsychopharmacology, 1989, Abstract, vol. 2, No. 2.

O'Neill, Timothy R., "Effects of Operating Practices on Commercial Driver Alertness" United States Office of Motor Carrier and Highway Safety, Trucking Research Institute, 1999, pp. 1-118.

Penetar et al., "Amphetamine Effects on Recovery Sleep Following Total Sleep Deprivation," Human Psychopharmacology, 1991, pp. 319-323, vol. 6.

Penetar et al., "Caffeine Reversal of Sleep Deprivation Effects on Alertness and Mood," Psychopharmacology, 1993, Abstract, pp. 359-365, vol. 112.

Penetar et al., "Effects of Caffeine on Cognitive Performance, Mood, and Alertness in Sleep-Deprived Humans," In B.M. Marriot (Ed.), Food Components to Enhance Performance, National Academy Press, Washington, DC, pp. 407-431.

Petz et al., "Studies of Psychophysiological and Temporal Conditions of Work," Archives of Industrial Hygiene and Toxicology, Dec. 1999, pp. 405-421, vol. 50, No. 4.

Priest, Dana, "War and Sleep," The Washington Post Magazine, Nov. 19, 2000, pp. 16-20, 26-28.

Proctor et al., "Effect of overtime work of cognitive function in automotive workers," Scandinavian Journal of Work, Environment & Health, Apr. 1996, pp. 124-132, vol. 22, No. 2.

Ray et al., "Coping and Other Predictors of Outcome in Chronic Fatigue Syndrome: A 1-Year Follow-Up," Journal of Psychosomatic Research, Oct. 1997, Abstract, pp. 405-415, vol. 43, No. 4.

Rechstschaffen et al., "A Manual of Standardized Technology, Techniques and Scoring System for Sleep Stages of Human Subjects," U.S. Department of Health, Education, and Welfare, Public Health Service—National Institutes of Health, 1968 (reprinted 1971), pp. 1-58.

U.S. Patent and Trademark Office, International Search Report, PCT/US2016/036532, dated Sep. 27, 2016.

U.S. Patent and Trademark Office, Written Opinion, PCT/US2016/036352, dated Sep. 27, 2016.

Avinash et al., "Parameter Estimation for a Biomathematical Model of Psychomotor Vigilance Performance Under Laboratory Conditions of Chronic Sleep Restriction," NSWO 16, 2005, Jan. 2005, pp. 39-42.

Biotechnology HPC Software Applications Institute (BHSAI), "2B-Alert Smartphone App," www.tartc.org, May 8, 2015, p. 1.

Rajdev et al., "A Unified Mathematical Model to Quantify Performance Impairment for Both Chronic Sleep Restriction and Total Sleep Deprivation," Journal of Theoretical Biology, vol. 331, Apr. 23, 2013, Elsevier Ltd., U.S., pp. 66-77.

Ramakrishnann et al., "A Biomathematical Model of the Restoring Effects of Caffeine on Cognitive Performance During Sleep Deprivation," Journal of Theoretical Biology, vol. 319, Nov. 23, 2012, Elsevier Ltd., U.S., pp. 22-33.

Ramakrishnan et al., "Dose-Dependent Model of Caffeine Effects on Human Vigilance During Total Sleep Deprivation," Journal of Theoretical Biology, vol. 358, May 20, 2014, Elsevier Ltd., U.S , pp. 11-24.

Ramakrishnann et al., "Modeling Individual Differences During Sleep Loss: Can a Mathematical Model Predict an Individual's Trait-Like Response to Both Total and Partial Sleep Loss?," Journal of Sleep Research, vol. 24, Jun. 2015, European Sleep Research Society, pp. 262-269.

Skeldon et al., "Mathematical Models for Sleep-Wake Dynamics: Comparison of the Two-Process Model and a Mutual Inhibition Neuronal Model," PLoS ONE, vol. 9, Issue 8, Aug. 2014, pp. 1-16.

\* cited by examiner

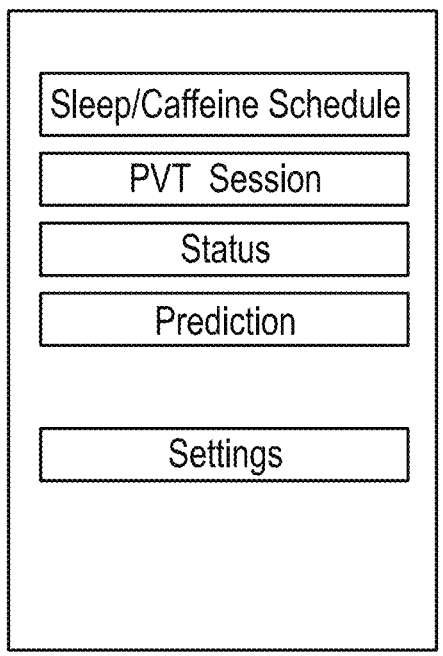
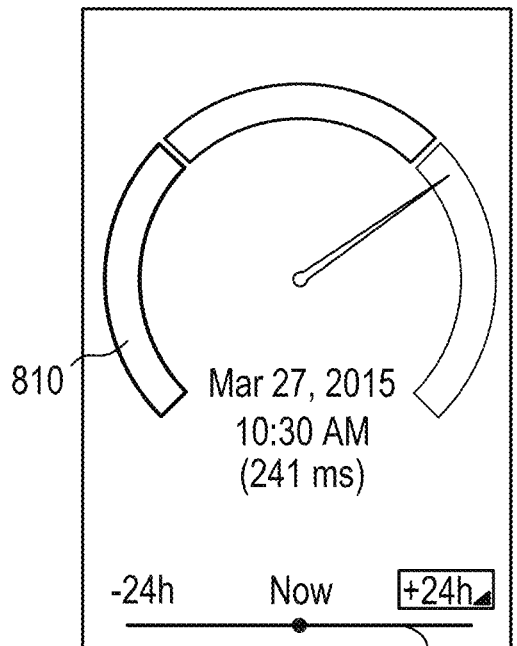

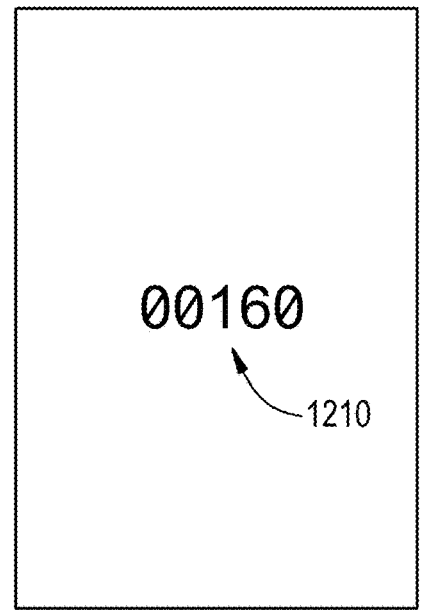
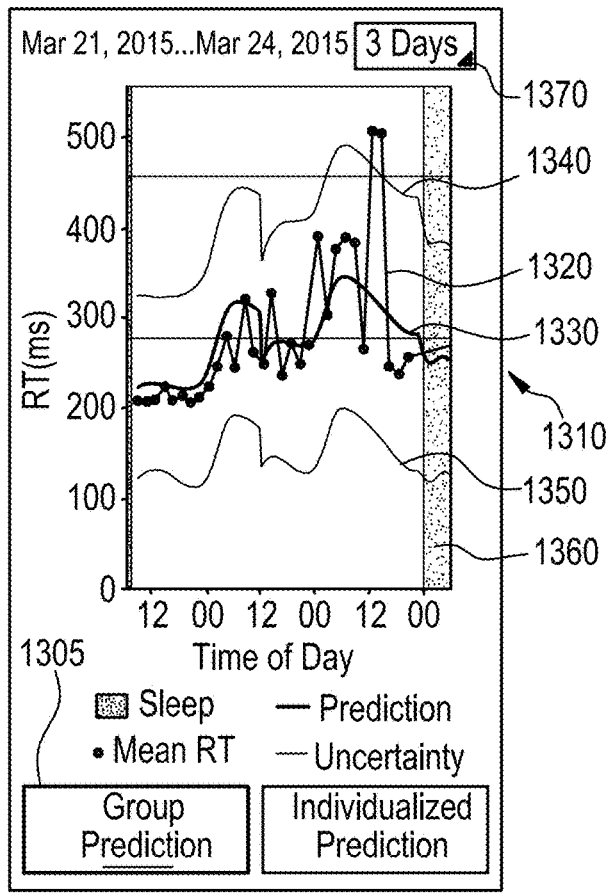
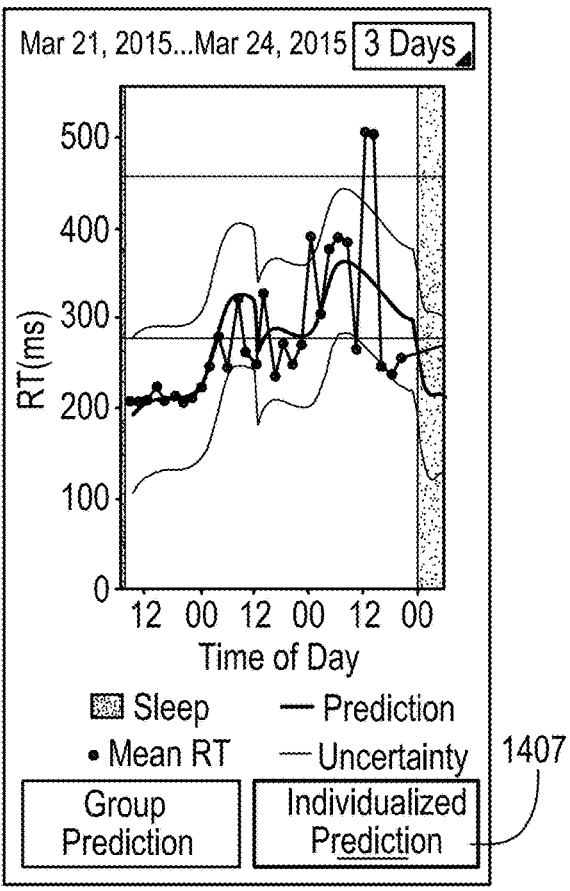
FIG. 11
FIG. 12
FIG. 13
FIG. 14

METHOD AND SYSTEM FOR MEASURING, PREDICTING, AND OPTIMIZING HUMAN COGNITIVE PERFORMANCE

This patent application is the National Stage Entry of International Application No. PCT/US2016/036532, filed on Jun. 8, 2016, which claimed the benefit of and priority to U.S. Patent Application No. 62/172,347 filed on Jun. 8, 2015, which is hereby incorporated by reference in its entirety.

I. FIELD OF THE INVENTION

At least one embodiment of this invention is intended to optimize human cognitive performance and alertness. In at least one embodiment, the system includes a portable computing device, such as a smartphone, and software that allows users to measure their current level of cognitive performance and alertness, and, in a further embodiment, make predictions about their future cognitive performance. In at least one embodiment, the cognitive performance is determined using a model with or without individualized parameters. In at least one embodiment, the system includes a plurality of portable computing devices and at least one server that is configured to communicate with portable computing devices continually and/or intermittently.

II. BACKGROUND OF THE INVENTION

Cognitive performance decrement due to sleep loss is recognized as a threat to safety and productivity in both civilian and military settings, prompting the investigation of pharmacological countermeasures against the adverse effects of reduced sleep on cognitive performance (Balkin et al., 2004; Caldwell and Caldwell, 2005). Among the various pharmacological sleep and fatigue countermeasures available, caffeine is the most widely used stimulant drug in both occupational and non-occupational settings. Over the past decade, results of numerous laboratory and field studies in which caffeine was administered as either a single or repeated dose have demonstrated that, when used at appropriate doses, caffeine can restore or maintain performance in sleep-deprived individuals, with minimal side effects (Bonnet et al., 2005).

The pharmacokinetics (PK) of caffeine and its dose-dependent metabolism in humans have been well characterized (Denaro et al., 1990) and the mechanism of action (antagonism of adenosine receptors) is also well-understood (Bertorelli et al., 1996). However, only very few attempts have been made to quantify or model the performance-enhancing effects of caffeine in humans and the applicant knows of no developed practical systems or applications for enhancing cognitive performance in the face of sleep deprivation using biomathematical models.

Substantial inter-individual variability exists with regard to response to sleep loss and is known to be trait-like (S. Ramakrishnan et al. 2015). This trait-like variability preferably is accounted for when modeling the effects of sleep loss and caffeine dosing in order to be effective in assessing and predicting the current and future states of a particular subject.

Over the past decade, computational tools have been increasingly used across a range of public and commercial sectors (e.g., aviation, mining, and nuclear power plant operations) as components of fatigue risk management systems aimed at optimizing duty-time alertness and thereby minimizing fatigue-related errors and accidents. These tools are based on biomathematical models that predict daily variations in neurobehavioral performance as a function of sleep/wake amounts and time of day. Such tools are particularly beneficial in industries that are engaged in 24-hour operations and require shift-work schedules. However, to date, there are no open-access tools available, and none of the commercially available tools contain biomathematical models that also predict the performance-improving effects of caffeine.

III. SUMMARY OF THE INVENTION

A system, method and apparatus in at least one embodiment includes a biomathetical model for optimizing cognitive performance in the face of sleep deprivation that integrates biomathematical models for quantifying performance impairment for both chronic sleep restriction and total sleep deprivation; the dose-dependent effects of caffeine on human vigilance; and the pheonotypical response of a particular user to caffeine dosing, chronic sleep restriction and total sleep deprivation in user-friendly software application which itself may be part of a networked system.

In at least one embodiment, the system includes a portable computing device, such as a smartphone, and software that allows users to measure their current level of cognitive performance and alertness, and make predictions about their future cognitive performance. The predictions can represent the alertness level of an "average" individual or can be customized, via an artificial intelligence (AI) algorithm, to represent the alertness of the user. Such predictions are based on the user's prior sleep history and caffeine consumption, which are provided by the user via a graphical interface. Sleep history can also be provided directly by a physiological-monitoring device, such as the wearable devices sold by Fitbit®, via wireless Bluetooth® technology or other wireless technologies. For customized predictions via the AI algorithm in at least one embodiment, users measure their cognitive performance and alertness multiple times over a period of days. In one scenario, the testing could be 4 or 5 times a day for about one week although other schedules are also possible as discussed in this disclosure. This allows the system to "learn" how changes in the user's sleep patterns and caffeine consumption affect the user's cognitive performance and alertness levels. In at least one embodiment, predictions of performance of an "average" individual, there is no need to measure cognitive performance of the user.

In at least one embodiment, users are also able to explore how future actions, such as naps, sleep/wake schedules, and timing and dosing of caffeine, would affect their future performance and alertness levels, thus allowing users to reach cognitive performance peaks and prolonged peak performance at the desired times.

The described embodiments include at least one embodiment having a number of substantial, novel and non-obvious improvements over the prior art, including but not limited to transforming physiological data, such as sleep history as well as the user's caffeine consumption data, into actionable information. In at least one embodiment, a system and process allows users to: 1) determine their current and future cognitive performance and alertness levels, and/or; 2) determine the appropriate dosage of future sleep schedules and caffeine consumption to modulate future cognitive performance and alertness.

In at least one embodiment, an electronic system is able to: 1) "learn" the user's phenotypical response to the continuum of sleep loss (from no sleep to partial sleep, including naps); 2) "learn" the user's phenotypical response to caffeine consumption; 3) "learn" the user's phenotypical response to the continuum of sleep loss and caffeine consumption based on measured cognitive performance data; 4) make user-specific (i.e., customizable) predictions of cognitive performance and alertness, while considering the effects of the continuum of sleep loss and caffeine consumption; 5) make group-average (i.e., "average") predictions of cognitive performance and alertness, while considering the effects of the continuum of sleep loss and caffeine consumption; 6) explore future sleep schedules to optimize future cognitive performance and alertness; and/or, 7) explore future caffeine consumption to optimize future cognitive performance and alertness.

In at least one embodiment, a system includes a user interface having a display and means for receiving input from the user; at least one motion detection sensor capable of detecting movement by an individual wearing the at least one motion detection sensor (in at least one embodiment, the motion detection sensor is an actigraph and/or an accelerometer); at least one memory configured to store a sleep model and data associated with the individual; and a processor in electrical communication with the user interface, the actigraph/accelerometer, the communications module, and the memory; the processor configured to receive a signal from the at least one motion detection sensor to monitor a level of activity of the user, store data obtained from the signal in the memory, when caffeine consumption information is received from the receiving means, store the caffeine consumption information in the memory as caffeine consumption data, determine an cognitive level for the user with the alertness model based on the stored data, the signal from the at least one motion detection sensor, and caffeine consumption data, and display the cognitive level on the display. In an alternative embodiment, the motion detection sensor is omitted and the sleep history data is provided by the user and/or the individual through the user interface. In a further embodiment, the system further includes upon request, predetermined schedule, when activity is detected or a combination of these, performing a response time test with the processor and the user interface; and wherein the processor is configured to perform the response time test by displaying a visual cue on the display, receiving an user response to the visual cue through the receiving means, calculating a response time, and repeating the displaying, receiving and calculating a plurality of times to determine a tested cognitive level; determine an offset between the model-determined cognitive level and the tested cognitive level; adjust at least one parameter weight in the alertness model based on the determined offset. In a further embodiment to any of the previous embodiments, the processor uses a Bayesian model or a recursive model in conjunction with a plurality of offsets to improve the alertness model fit to the individual.

In a further embodiment to the above embodiments, the system further includes a server and the processor transmits the alertness model weights to a server. In a further embodiment to any of the embodiments of the previous paragraph, the system includes multiple devices based on those embodiments and wherein the server capable of electrical communication with the processor, the server configured to receive alertness model weights from the processor, store received alertness model weights in a database associated with the user of the computing device that sent the alertness model weights, and provide a planning interface to model different timing and amounts of sleep and caffeine consumption to provide a forecast for future cognitive levels or a regression for past cognitive levels for the user associated with the alertness model weights. In a further embodiment, the server is configured to analyze user data including user activity history, cognitive levels, caffeine consumption and weights to develop a new set of weights for future users matching a profile of current users. In a further embodiment to the other embodiments in this paragraph, the server displays the forecast or the regression for a plurality of users to allow for work schedule planning. In a further embodiment to the other embodiments in this paragraph, the server configured to receive a future time that an optimal cognitive level is desired, receive at least one restriction regarding sleep or caffeine consumption, run a plurality of models with different caffeine consumptions and sleep using the at least one received restriction, and display the plurality of results from the model runs. In a further embodiment to the other embodiments in this paragraph, the server configured to receive projected sleep time and/or caffeine consumption for a particular user and project a future cognitive level using the project sleep time and/or caffeine consumption for the user. In a further embodiment of this paragraph, the server provides a preset menu selection on the display as the receiving means, the preset menu selection includes entries for types and/or amounts of caffeine consumed.

In a further embodiment to the previous embodiments, the processor displays an alertness gauge on the display to show the user a graphical representation of their current cognitive level relative to at least one benchmark cognitive levels. In a further embodiment to the previous embodiments, the processor provides a preset menu selection on the display as the receiving means, the preset menu selection includes entries for types and/or amounts of caffeine consumed.

In a further embodiment to the previous embodiments, alertness model includes $$P_c(t) = (S(t) + \kappa C(t)) * g_{PD}(t, c)$$

where $$C(t) = \sum_{i=1}^{5} a_i \sin\left[i\frac{2\pi}{\tau}(t + \Phi)\right]$$

where $a_1=0.97$, $a_2=0.22$, $a_3=0.07$, $a_4=0.03$, and $a_5=0.001$, $\tau$ denotes the period of the circadian oscillator, and $\Phi$ denotes the circadian phase, and $$S(t) = \begin{cases} U - (U - S_0)\exp(-t/\tau_w) & \text{during wakefulness} \\ -2U + (2U + S_0)\exp(-t/\tau_s) + (2U + L_0) & \text{during sleep} \\ [\tau_{LA}/(\tau_{LA} - \tau_s)][\exp(-t/\tau_{LA}) - \exp(-t/\tau_s)] \end{cases}$$

where U and L denote the upper and lower asymptotes of process S, respectively, $\tau_w$ and $\tau_s$ denote the time constants, and $\tau_{LA}$ denotes the time constant of the exponential decay of the effect of sleep history on cognitive performance, where $$L(t) =$$

$$\begin{cases} \max[U - (U - L_0)\exp(-t/\tau_{LA}), -0.11U] & \text{during wakefulness} \\ \max[-2U + (2U + L_0)\exp(-t/\tau_{LA}), -0.11U] & \text{during sleep} \end{cases}$$

where

-continued $$g_{PD}(t, c) = \left[1 + M_c \frac{k_a}{k_a - k_c} \{\exp[-k_c(t - t_0)] - \exp[-k_a(t - t_0)]\}\right]^{-1}$$

for $t \geq t0$ $M_c = M_0 \cdot c$ and $k_c = k_0 \exp(-z \cdot c)$ where $M_c$ and $k_c$ denote the amplitude factor and elimination rate for a caffeine dose c administered at time $t_0$, $M_0$, $k_0$, $z$, and $k_a$ denote the amplitude slope, basal elimination rate, decay constant, and absorption rate. In a further alternative embodiment, parameter weights for $\tau_w$, $\tau_s$, $\varphi$, $\kappa$, and $\tau_{LA}$ are adjustable.

In a further embodiment to the previous embodiments, the receiving means is configured to receive a future time from the user, and the processor configured to project the cognitive level at the future time assuming the user is awake between now and the future time. In a further embodiment to the previous embodiments, the receiving means is configured to receive a future time from the user, and the processor configured to project the cognitive level at the future time where the user is projected as maintaining recent sleep patterns between now and the future time where recent sleep patterns are based on stored activity data. In a further embodiment to the previous embodiments, the device with the processor and the memory is a smartphone or a tablet. In a further embodiment to the previous embodiments, the system further includes a communications module in communication with the processor. In a further embodiment to the previous embodiment, the communications module includes at least one of a transmitter, an antenna, a receiver, a transreceiver, a light source, a light sensor, a plug, and a connector. In a further embodiment to the previous embodiments, wherein the user and the individual are the same person. In a further embodiment to the previous embodiments, wherein the motion detection sensor is located in a wrist-worn device; and the user interface, the at least one memory, and the processor are located in a separate device capable of communication with the wrist-worn device. In a further embodiment to the previous embodiments, user interface includes at least one item selected from a group consisting of a display, a touchscreen, at least one light, a speaker, a transducer, at least one button, at least one switch, at least one touchpad, a keyboard, an external accessory, a communications module, and a microphone.

In at least one embodiment, a system includes: a plurality of computing devices where each computing device is assigned to an individual, each of the computing devices having a user interface having a display and means for receiving input from the user; at least one motion detection sensor capable of detecting movement by an individual wearing the at least one motion detection sensor; at least one memory configured to store a sleep model and data associated with the individual; and a processor in electrical communication with the user interface, the actigraph/accelerometer, the communications module, and the memory; the processor configured to receive a signal from the at least one motion detection sensor to monitor a level of activity of the user, store data obtained from the signal in the memory, when caffeine consumption information is received from the receiving means, store the caffeine consumption information in the memory as caffeine consumption data, determine an cognitive level for the user with the alertness model based on the stored data, the signal from the at least one motion detection sensor, and caffeine consumption data, and display the cognitive level on the display, a server capable of at least intermittent communication with each of the plurality of computing devices, the server configured to receive alertness model weights from the processors, store received alertness model weights in a database associated with the individual associated with the computing device that sent the alertness model weights, and provide a planning interface to model different timing and amounts of sleep and caffeine consumption to provide a forecast for future cognitive levels or a regression for past cognitive levels for the user associated with the alertness model weights. In a further embodiment, the server is configured to analyze user data including user activity history, cognitive levels, caffeine consumption and weights to develop a new set of weights for future users matching a profile of current users. In a further embodiment, the server displays the forecast or the regression for a plurality of users to allow for work schedule planning. In a further embodiment to the other embodiments of this paragraph, the server configured to receive a future time that an optimal cognitive level is desired, receive at least one restriction regarding sleep or caffeine consumption, run a plurality of models with different caffeine consumptions and sleep using the at least one received restriction, and display the plurality of results from the model runs. In a further embodiment to the other embodiments of this paragraph, the server configured to receive projected sleep time and/or caffeine consumption for a particular user and project a future cognitive level using the project sleep time and/or caffeine consumption for the user. In a further embodiment to the other embodiments of this paragraph, the computing device performing a response time test with the processor and the user interface; and wherein the processor is configured to perform the response time test by displaying a visual cue on the display, receiving an user response to the visual cue through the receiving means, calculating a response time, and repeating the displaying, receiving and calculating a plurality of times to determine a tested cognitive level; determine an offset between the model-determined cognitive level and the tested cognitive level; adjust at least one parameter weight in the alertness model based on the determined offset. In a further embodiment to the other embodiments of this paragraph, the processor uses a Bayesian model or a recursive model in conjunction with a plurality of offsets to improve the alertness model fit to the individual.

In at least one embodiment, a method for determining an individual's cognitive state using a computing device having a processor, a memory, a motion detection sensor, a display, and a receiving means for receiving input from a user about the individual, the method including: receiving a signal from the at least one motion detection sensor configured to monitor a level of activity of the user, storing data obtained from the signal in the memory, when caffeine consumption information is received from the receiving means, storing the caffeine consumption information in the memory as caffeine consumption data, determining an cognitive level for the user with the alertness model based on the stored data, the signal from the at least one motion detection sensor, and caffeine consumption data, and displaying the cognitive level on the display. In a further embodiment, the method further including: performing a response time test with the processor, the display and the receiving means, where preforming a response time test includes displaying a visual cue on the display, receiving an user response to the visual cue through the receiving means, calculating a response time, and repeating the displaying, receiving and calculating a plurality of times to determine a tested cognitive level; determining an offset between the model-determined cognitive level and the tested cognitive level; adjusting at least one parameter weight in the alertness model based on the determined offset. In a further embodiment to the previous method embodiments, the method further includes using a Bayesian model or a recursive model in conjunction with a plurality of offsets to improve the alertness model fit to the individual. In a further embodiment to the previous method embodiments, the method further includes providing a future cognitive level by using a sleep history provided by the user, a projected sleep history based on recent sleeping patterns such that an average bedtime and an average wake time are used to determine when sleep will occur, and/or assumption that no sleep will occur between a current time and the time for the future cognitive level.

The various features of novelty that characterize at least one embodiment are pointed out with particularity in the claims annexed to and forming a part of this disclosure. For a better understanding of the invention, operating advantages and specific objects attained by use of at least one embodiment, reference is made to the accompanying drawings and descriptive matter in which a preferred embodiment of the invention is illustrated.

IV. BRIEF DESCRIPTION OF THE DRAWINGS

FIG. 7 illustrates a home-page graphical user interface display according to at least one embodiment.

FIG. 8 illustrates a graphical user interface display relaying information on alertness levels.

FIG. 9 illustrates a graphical user interface display relaying a user sleep log.

FIG. 10 illustrates a graphical user interface display relaying user caffeine dosing input functionality.

FIG. 11 illustrates a graphical user interface display relaying a user caffeine dosing log.

FIG. 12 illustrates a graphical user interface display relaying a visual reaction time PVT test.

FIG. 13 illustrates a graphical user interface display relaying the results of a prediction of cognitive performance using group statistics.

FIG. 14 illustrates a graphical user interface display relaying the results of a prediction of cognitive performance using individual statistics.

V. DETAILED DESCRIPTION

Figure 1A:
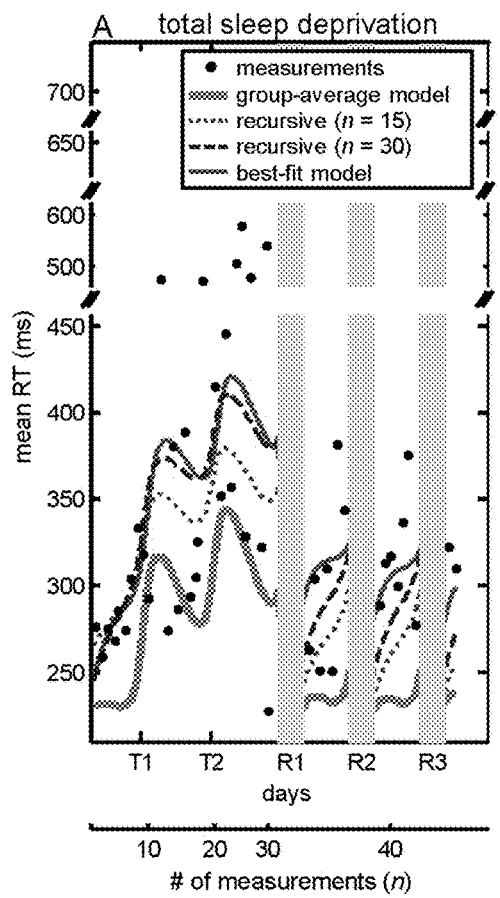
FIGS. 1A-1D show measured Psychomotor Vigilance Task (PVT) performance data along with the results for the best-fit model, group-average model, and recursive algorithm for adjusting the model for two subjects.

To aid in understanding at least one embodiment of the invention, several terms are defined at this point.

The terms "response," "outcome" or "dependent variable" are used for measurements that are free to vary in response to other variables called "predictor variables," "independent variables" or "explanatory variables".

Dependent and independent variables may be measured using the following nomenclature:

"Nominal Variables": binary, dichotomous or binomial discrete variables consisting of only two categories. Variables comprising more than two distinct sets of categories are called "multinomial" or "polytomous".

"Ordinal Variables": variables describing discrete, categorical, qualitative data that are organized by natural or ranked order that could include count or frequency per category data.

"Continuous Variables": variables whose measurements fall on a continuous scale that could include both interval and ratio scale measurements or other quantitative data. Continuous Variables are also known as "covariates".

A "Factor" is a qualitative, explanatory variable whose categories are subdivided into levels.

As used herein, the terms "coefficients" and "coefficient values," unless otherwise explicitly specified, are intended to include within their scope that only coefficients, but also any constant or other terms that may be necessary for a model. Such terms may include, for example, an intercept term, a mean squared error term, and/or a number of degrees or freedom term. In addition, "coefficient" data, as used herein, also includes, unless explicitly stated, data computed "on-the-fly" from one or more parent parameters (e.g., the data is computed as a function of and other parameter that is retrieved from a database or requested as input).

The term "PVT" means psychomotor vigilance task which includes, but is not limited to a simple (one choice) reaction-time task in which subjects press a button in response to a visual stimulus that is presented on a random interval (2-10 seconds) schedule over a 10-minute period, resulting in ~100 stimulus-response pairs (Dorrian et al., 2005). It may also include mathematical processing, running memory, and visual analogue scale of fatigue.

The phrase "chronic sleep restriction" or "CSR" means instances of sustained periods of time with suboptimal sleep, for example 7, days of 3 hours nightly time in bed although different lengths and number of hours of nightly sleep are possible as one of ordinary skill in the cognitive/sleep field would understand this phrase.

The phrase "total sleep deprivation" or "TSD" means periods of acute instances where a subject has no sleep, for example no sleep for a period of 64 hours although different lengths are possible as one of ordinary skill in the cognitive/sleep field would understand this phrase.

At least one embodiment is directed at a system and method for determining a cognitive level of an individual using a model taking into account circadian and homeostatic processes along with caffeine consumption of the individual. In a further embodiment, the variable (or parameter) weights in the model are adjusted for a particular individual based on results of at least one PVT test. In a still further embodiment, the system communicates with a server (or central processing system) to provide for planning including for the individual and a group of individuals such as a workforce.

The model assumes for caffeine-free performance that the temporal pattern of alertness can be represented as the additive interaction of two separate processes: (1) the homeostatic process S, which rises monotonically during wakefulness and declines monotonically during sleep (Daan et al., 1984) and (2) a circadian process C, which is a 24-hour periodic, self-sustaining oscillator modeled as a five-harmonic sinusoidal equation. When the model includes caffeine, a caffeine effect acts as a multiplicative effect. In at least one embodiment, the model is as follows:

$$P_c(t) = (S(t) + \kappa C(t)) * g_{PD}(t,c) \quad (1)$$

where C and S denote the circadian and homeostatic processes of the two-process model at time t, respectively, and $\kappa$ represents the circadian amplitude. The $g_{PD}$ denotes the caffeine effect based at least on time and consumption and PD denotes the Pharmacodynamic of caffeine.

Process C (circadian) in at least one embodiment is independent of sleep/wake history and represents a self-sustaining oscillator with a 24-hour period. The circadian process C in at least one embodiment is as follows:

$$C(t) = \sum_{i=1}^{5} a_i \sin\left[i \frac{2\pi}{\tau}(t + \phi)\right] \quad (2)$$

where $\alpha_i$, $=1, \ldots, 5$, represent the amplitude of the five harmonics ($a_1=0.97$, $a_2=0.22$, $a_3=0.07$, $a_4=0.03$, and $a_5=0.001$), $\tau$ denotes the period of the circadian oscillator (~24 hours), and $\Phi$ denotes the circadian phase.

Process S (sleep homeostasis) in at least one embodiment is dependent on the individual's sleep/wake history, increases exponentially with time awake and decreases exponentially with sleep/recovery time to a basal value, whose rates of increase/decrease are individual-specific, assumed to be constant, and have unknown values. The homeostatic process S in at least one embodiment is as follows:

$$S(t) = \begin{cases} U - (U - S_0)\exp(-t/\tau_w) & \text{during wakefulness} \\ -2U + (2U + S_0)\exp(-t/\tau_s) + \\ (2U + L_0)[\tau_{LA}/(\tau_{LA} - \tau_s)] \\ [\exp(-t/\tau_{LA}) - \exp(-t/\tau_s)] & \text{during sleep} \end{cases} \quad (3)$$

where U and L denote the upper and lower asymptotes of process S, respectively, $\tau_w$ and $\tau_s$ denote the time constants of the increasing and decreasing sleep pressure during wakefulness and sleep, respectively, and $\tau_{LA}$ denotes the time constant of the exponential decay of the effect of sleep history on performance. $S(0)=S_0$ and $L(0)=L_0$ correspond to the initial state values for S and L, respectively.

In at least one embodiment, the model incorporates sleep debt into the two-process model by describing changes in an individual's capacity to recover during sleep as a function of Debt(t), i.e., the lower asymptote L(t) of the homeostatic process is allowed to increase or decrease with increased or decreased Debt(t), respectively, while the upper asymptote U remains constant in at least one embodiment.

The values of L(t) during sleep and wake were chosen so that if an individual sleeps 8 hours, the recommended optimum sleep time per night, the area under the curve (AUC) for L(t) over a 24-hour period is equal to zero (16×1+(−2)×8). In the differential equation defining the dynamics of Debt(t), sleep losses or sleep extensions that occurred in the remote past have a much weaker influence on the present sleep debt than comparable events in the more recent past. For an individual restricted to 8-hours time in bed (TIB) each day, the AUC for Loss(t) each day would be zero, and the lower asymptote L(t) would oscillate around zero, reaching its highest point before bed-time and its lowest point at awakening. If the time constant $\tau_{LA}$ is slow (e.g., $\tau_{LA}$=120 hours), the magnitude of this oscillation would be 0.06 U, and thus the model would closely approximate Borbelys two-process model.

To initialize the model in at least one embodiment, Debt(0) is set to any value between −2 and 1, which ensures that Debt(t) lies in this range for all t>0. Although in at least one embodiment, the Debt(0) is set based upon the recent sleep history for the individual being monitored.

The lower asymptote L of process S:

$$L(t) = \begin{cases} \max[U - (U - L_0)\exp(-t/\tau_{LA}), -0.11U] & \text{during wakefulness} \\ \max[-2U + (2U + L_0)\exp(-t/\tau_{LA}), -0.11U] & \text{during sleep} \end{cases} \quad (4)$$

In at least one embodiment, the above model processes include a total of eight parameters: S(0), U, L(0), $\tau_w$, $\tau_s$, $\varphi$, $\kappa$, and $\tau_{LA}$.

The caffeine effect ($g_{PD}$):

$$g_{PD}(t, c) = \left[1 + M_c \frac{k_a}{k_a - k_c}\{\exp[-k_c(t - t_0)] - \exp[-k_a(t - t_0)]\}\right]^{-1} \quad (5a)$$

for $t \geq t0$ $$M_c = M_0 \cdot c \text{ and } k_c = k_0\exp(-z \cdot c) \quad (5b)$$

where $M_c$ and $k_c$ denote the amplitude factor and elimination rate for a caffeine dose c administered at time $t_0$, respectively. $M_0$, $k_0$, z, and $k_a$ denote an amplitude slope, a basal elimination rate, a decay constant, and an absorption rate, respectively.

In order to model repeated caffeine doses, Eq. (5a) is modified to allow for an adjustment of the amplitude factor and the elimination rate on extant plasma caffeine concentration. Accordingly, the PD effect after j doses of caffeine of strengths $D_1, D_2, \ldots, D_j$ administered at discrete-time indices $t_1, t_2, \ldots, t_j$, respectively, can be expressed as follows:

$$g_{PD}(t, D_j) = \begin{cases} 1 & \text{for } t < t_1 \\ (1 + M_{Dj}\exp[-k_{Dj}T_s(t - t_j)])^{-1} & \text{for } t \geq t_j, j = 1, 2, \ldots \end{cases} \quad (6)$$

where $M_{Dj}$ and $k_{Dj}$ denote the effective amplitude factor and elimination rate parameters, respectively, that depend on the caffeine concentration at time $t_j$.

Using Eq. (6), these parameters can be expressed as follows:

$$M_{Dj} = M_0 \times [D_j + E(t_j^-)] \text{ and } k_{Dj} = k_0 \exp\{-z[D_j + E(t_j^-)]\} \quad (7)$$

where $E(t_j^-)$ is the equivalent caffeine dose representing the caffeine concentration present at time $t_j$ immediately prior to the administration of dose $D_j$. The expression for $E(t_j^-)$ follows from the standard one-compartment PK model:

$$E(t_j^-) = \begin{cases} 0 & \text{for } j = 1 \\ [E(t_{j-1}^-) + D_{j-1}]\exp[-k_{Dj}T_s(t_j - t_{j-1})] & \text{for } j = 2, 3, \ldots \end{cases} \quad (8)$$

The repeated-dose model in Eq. (6) reduces to Eq. (5a) under single dose conditions. However, the model in Eq. (6) assumes that: (1) each of the repeated caffeine doses are administered via the same formulation and (2) $g_{PK50}$ of the Hill equation, which affects the amplitude slope $M_0$, remains constant with repeated doses.

In at least one embodiment, an example of the beginning parameter values (standard errors) for both lapse and mean response time (RT) statistics are shown in the table below.

| Parameter | Lapse | Mean RT |
|---|---|---|
| U | 18.4 (0.7) lapses | 497 (31) ms |
| $\tau_w$ | 40.0 (3.2) h | 23.0 (3.2) h |
| $\tau_s$ | 2.1 (0.1) h | 4.0 (1.0) h |
| $S_0$ | 0.5 (0.7) lapses | 176 (15) ms |
| $\kappa$ | 3.3 (0.3) lapses | 75 (7) ms |
| $\phi$ | 2.3 (0.3) h | 2.5 (0.2) h |
| $\tau_{LA}$ | 7.0 (1.7) d | 7.0 (2.6) d |
| $L_0$ | 0.0 (0.0) lapses | 140 (14) ms |
| $M_0$ | 9.86 (1.80) $g^{-1}$ | 3.59 (0.66) $g^{-1}$ |
| $k_0$ | 0.49 (0.17) $h^{-1}$ | 0.49 (0.17) $h^{-1}$ |
| Z | 1.63 (1.61) $g^{-1}$ | 1.63 (1.61) $g^{-1}$ |
| $k_a$ (capsule) | 2.06 (0.36) $h^{-1}$ | 2.06 (0.36) $h^{-1}$ |
| $k_a$ (gum)[21] | 3.21 (0.78) $h^{-1}$ | 3.21 (0.78) $h^{-1}$ |

In at least one embodiment, different types of caffeine sources have different absorption rates $k_a$ for use in alternative embodiments, where the user selects (or indicates) the type and amount of the caffeine being ingested.

In at least one embodiment, the system and/or method adjust the above variable weights based on PVT testing. There are different approaches for how the system may perform the adjustments, including post hoc individualization, Bayesian learning, and real-time recursive model individualization.

a. Post Hoc Individualization

One approach to individualizing the model is by fitting the model parameters $\theta$ to a set of PVT measurements accumulated over time and available for the individual. In this post hoc approach, the system learns an individual's trait-like response to sleep loss en masse by minimizing the sum of squared errors between the accumulated set of N PVT measurements $y_i$, with $i = 1, 2, \ldots, N$, and the corresponding model predicted performance $f(t_i, \theta)$ using Eq. (1), at discrete times $t_i$, as follows:

$$\underset{\theta}{\mathrm{argmin}}\left\{\sum_{i=1}^{N}[y_i - f(t_i, \theta)]^2\right\} \quad (9)$$

The solution of Eq. (9) leads to a "best-fit" model, with more optimal parameters $\theta^*$. Such a post hoc approach allows for the identification of model parameters through well-established optimization routines and yields accurate estimates of $\theta$ when an accumulated set of PVT measurements is used for the optimization, such as at the conclusion of a study or a period of time has lapsed. However, it can lead to unreliable estimates of $\theta$ when the number of measurements are too few, making it less useful for real-time, on the fly model individualization.

b. Bayesian Learning

Bayesian learning can be used to address the limitations of post hoc, and it allows for more reliable model individualization as each new PVT performance measurement becomes available. In Bayesian learning, it is assumed that an individual's parameters $\theta$ can be progressively and incrementally learned from the combination of an original set of (prior) mean parameters $\theta_0$ representative of an "average" individual and the individual's own set of n PVT measurements $y_i$, with $i = 1, 2, \ldots, n$, up to the current time $t_n$ (where $n \leq N$). This is achieved by solving the following nonlinear optimization problem:

$$\underset{\theta}{\mathrm{argmin}}\left\{(\theta - \theta_0)^T \Sigma_0^{-1}(\theta - \theta_0) + \frac{1}{\sigma^2}\sum_{i=1}^{n}[y_i - f(t_i, \theta)]^2\right\} \quad (10)$$

where $\Sigma_0$ represents the prior variance-covariance matrix of the model parameters $\theta_0$, and $\sigma^2$ represents the noise variance in PVT measurements $y_i$. The first term in Eq. (10) represents the deviation of the model parameters from those of the average individual (i.e., the prior information in at least one embodiment), and the second term represents the residual of the model fit to the n available measurements, as in Eq. (9). When only a few measurements are available (i.e., when n is small), the solution of Eq. (10) is largely weighted by the first term, leading to individualized models that are very similar to the average individual's model. However, as n grows larger, the weight shifts to the second term, leading to individualized models that represent the individual's sleep-loss phenotype. In the extreme case where $n \to \infty$, the model obtained by optimizing Eq. (10) converges asymptotically to the model obtained by directly fitting to the measurements alone, i.e., the best-fit model obtained by solving Eq. (9).

c. Real-Time Recursive Model Individualization

An alternative approach to obtain $\theta$ and individualize the model in a computationally efficient manner without the need to store a history of PVT measurements and perform nonlinear optimization is to approximate the solution to the Bayesian optimization problem in Eq. (10). Using an extended Kalman filter formulation, the model parameters $\hat{\theta}_n$ can be recursively estimated, at the current time $t_n$, with $n=1, 2, \ldots, N$, as a function of the previous estimate $\hat{\theta}_{n-1}$ at time $t_{n-1}$ and the current PVT measurement $y_n$, by solving the following algebraic equations:

$$\hat{\theta}_n = \hat{\theta}_{n-1} + \frac{\hat{\Sigma}_{n-1} J_n}{\sigma^2 + J_n^T \hat{\Sigma}_{n-1} J_n} [y_n - f(t_n, \hat{\theta}_{n-1})] \quad (11)$$

$$\hat{\Sigma}_n = \left(I - \frac{\hat{\Sigma}_{n-1} J_n J_n^T}{\sigma^2 + J_n^T \hat{\Sigma}_{n-1} J_n}\right) \hat{\Sigma}_{n-1}, \quad (12)$$

where $\hat{\Sigma}_n$ and $\hat{\Sigma}_{n-1}$ denote the estimated variance-covariance matrix of the model parameters at times $t_n$ and $t_{n-1}$, respectively, $J_n = \partial f(t_n, \theta)/\partial \theta|_{\theta = \hat{\theta}_{n-1}}$ represents the Jacobian of the model output with respect to the model parameters at time $t_n$, and I represents the identity matrix. The approximate nature of the estimate $\hat{\theta}_n$ stems from the first-order Taylor series expansion used to compute the Jacobian $J_n$ of the nonlinear function $f(t_n, \theta)$ in Eq. (1).

The recursion starts by solving for $\hat{\theta}_1$ and $\hat{\Sigma}_1$, assuming that $\hat{\theta}_0 = \theta_0$ and $\hat{\Sigma}_0 = \Sigma_0$, where $\theta_0$ and $\Sigma_0$ denote priors as in Eq. (10). Specifically, nonlinear mixed-effect modeling is used to estimate the group-average model parameters and the corresponding variance-covariance matrix for the model using our study data, and assigned them to $\theta_0$ and $\Sigma_0$, respectively. To ensure that the prior $\theta_0$ and $\Sigma_0$ did not contain information about the subject to be predicted, that subject is excluded from the sample and estimated $\theta_0$ and $\Sigma_0$ using data from other subjects in the study.

The confidence intervals (CIs) of the model parameters and the prediction intervals of the model output at the current time $t_n$ are computed. To this end, it is assumed that the model parameters (model outputs) asymptotically followed a multivariate Gaussian distribution with mean $\hat{\theta}_n[f(t, \hat{\theta}_{n-1})]$ and variance-covariance matrix $\hat{\Sigma}_n[J^T\hat{\Sigma}_n J+\sigma^2]$.

Because the model output has been shown to be insensitive to the three time constants $\tau_w$, $\tau_s$, and $\tau_{LA}$, these parameters in this embodiment were set to $\tau_w=18.2$ hours, $\tau_s=4.2$ hours, and $\tau_{LA}=7$ days. Therefore, for each subject only five model parameters: $\theta=[U, \kappa, \phi, S_0, L_0]$ were estimated.

As an individual's PVT performance data accumulate and $n \to \infty$, the recursive learning algorithm in Eq. (11) is expected to yield model parameters and model predictions that progressively approach the best-fit model in Eq. (9) and its predictions.

d. Testing of the Recursive Learning Algorithm

To assess the ability of the recursive learning algorithm to yield accurate model predictions (i.e., outputs) after n PVT measurements, the root mean squared error (RMSE) is computed between the predictions and the measurements. The RMSE is computed for the best-fit model to assess the ability of the model to fit the complete set of N measurements. In addition, to compare the model predictions produced by parameters estimated by the recursive algorithm after n measurements with the model fitting produced by parameters estimated by the best-fit model using N measurements, with $n \leq N$, the relative RMSE, defined as the difference in RMSEs between the recursively learned model and the best-fit model divided by the RMSE of the best-fit model is computed as follows:

$$\text{relative } RMSE = \frac{\sqrt{\frac{1}{N}\sum_{i=1}^{N}[y_i - f(t_i, \hat{\theta}_n)]^2} - \sqrt{\frac{1}{N}\sum_{i=1}^{N}[y_i - f(t_i, \theta^*)]^2}}{\sqrt{\frac{1}{N}\sum_{i=1}^{N}[y_i - f(t_i, \theta^*)]^2}} \times 100\%. \quad (13)$$

In the analyses to follow, the model described above was assessed by simulating real-time performance using a cross-over-design study involving 18 subjects challenged with both 64 hours of TSD and 7 days of CSR of 3 hours TIB per night, using PVT data measured every 2 hours during wakefulness. The real-time performance was simulated by sequentially providing each of the N PVT measurements to the recursive algorithm, updating the model parameters after each measurement, and using the updated model to obtain performance predictions for an individual. These results were compared with those obtained with the best-fit model, which fitted the model parameters using each individual's complete set of PVT measurements (N=51 for the TSD and N=85 for the CSR). Also, unless noted otherwise, we assessed PVT performance using mean RT statistics.

e. Convergence of the Recursive Algorithm

Figure 1B:
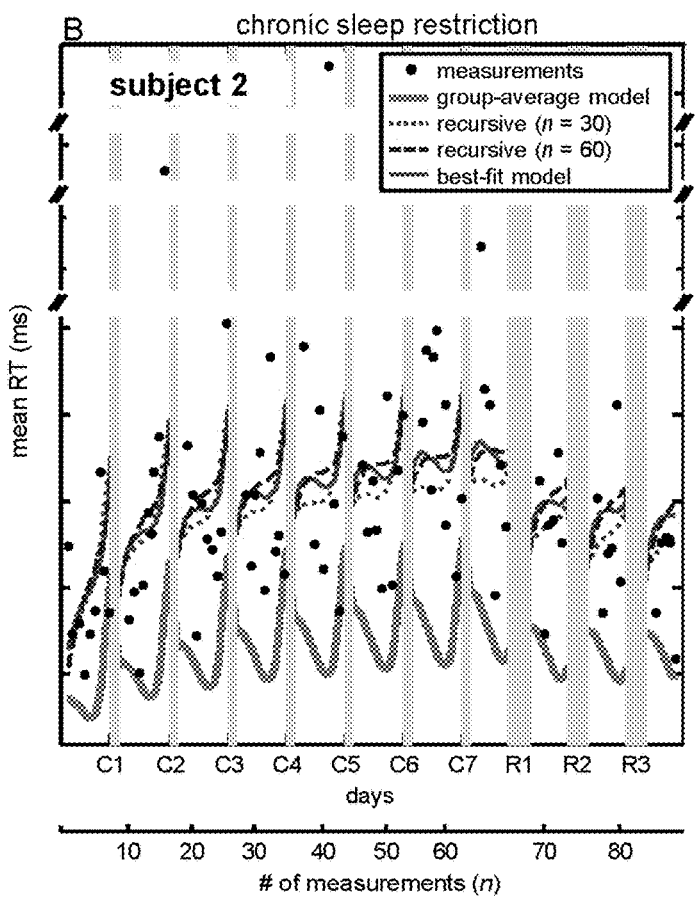
Figure 1C:
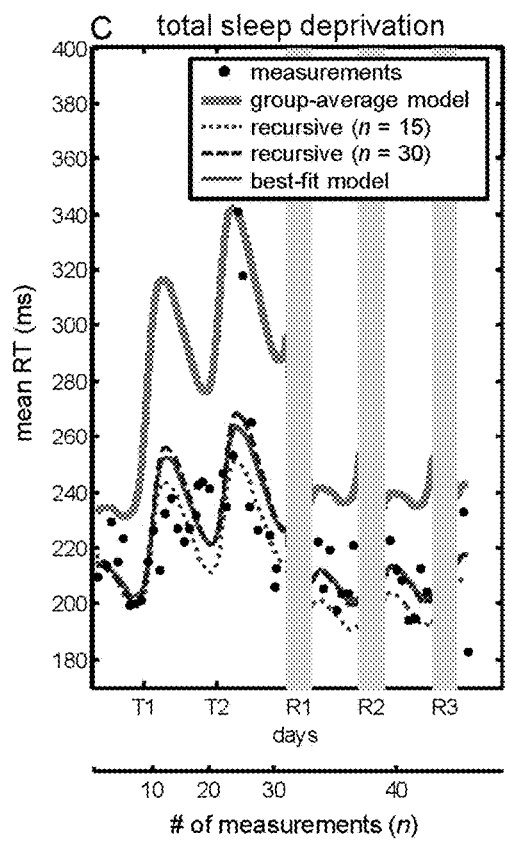
Figure 1D:
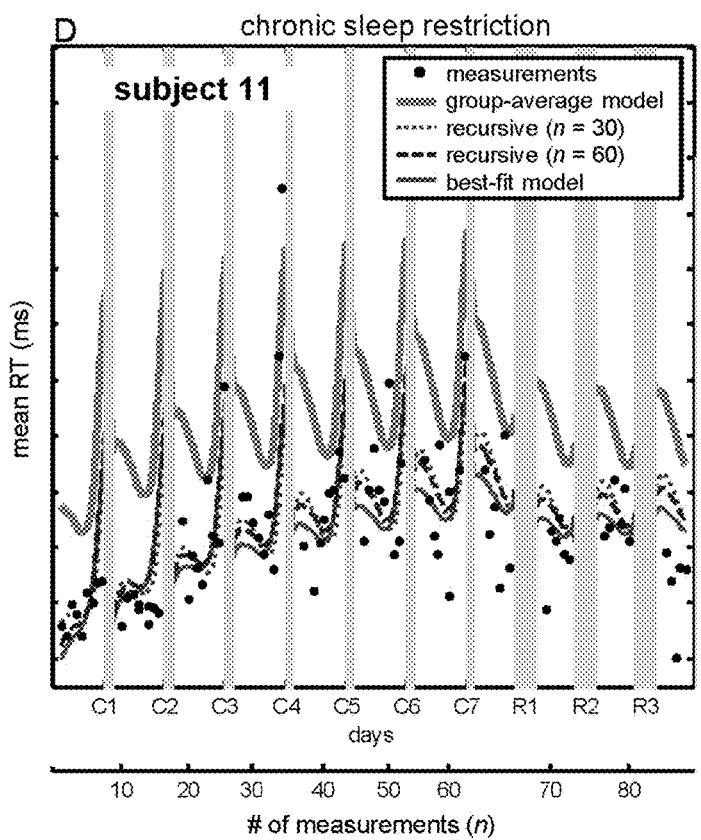
Figure 2A:
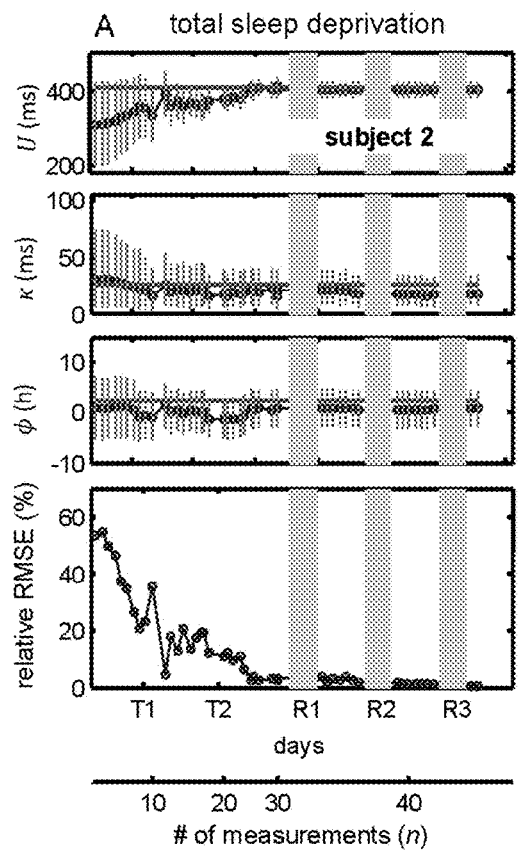
FIGS. 2A-2D show corresponding values of the recursive algorithm estimates for the three most sensitive model parameters with their associated confidence intervals (CI), the best-fit model parameters, and the relative the root mean squared errors (RMSEs) as a function of PVT measurements.
Figure 2B:
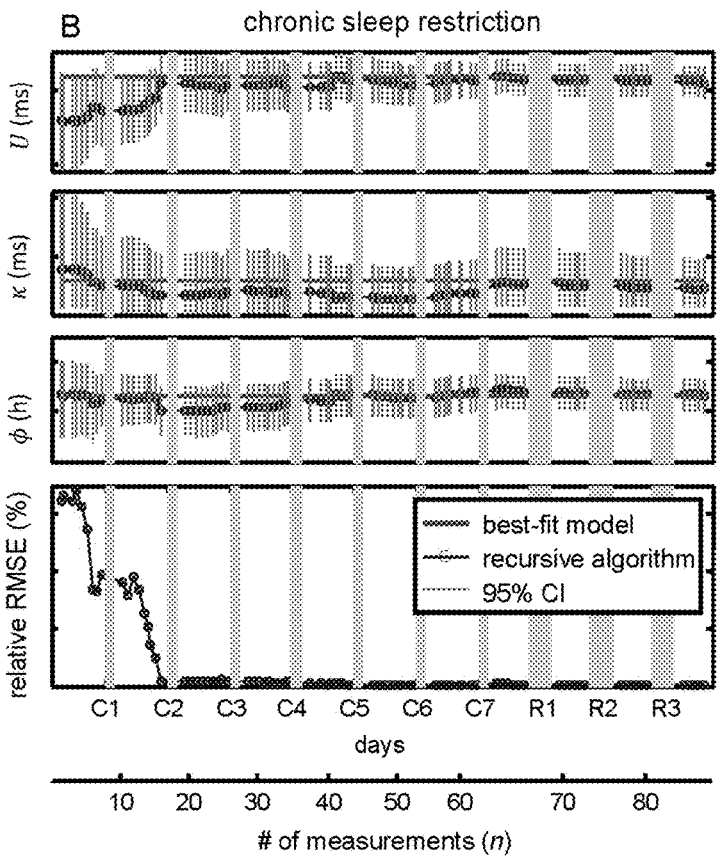
Figure 2C:
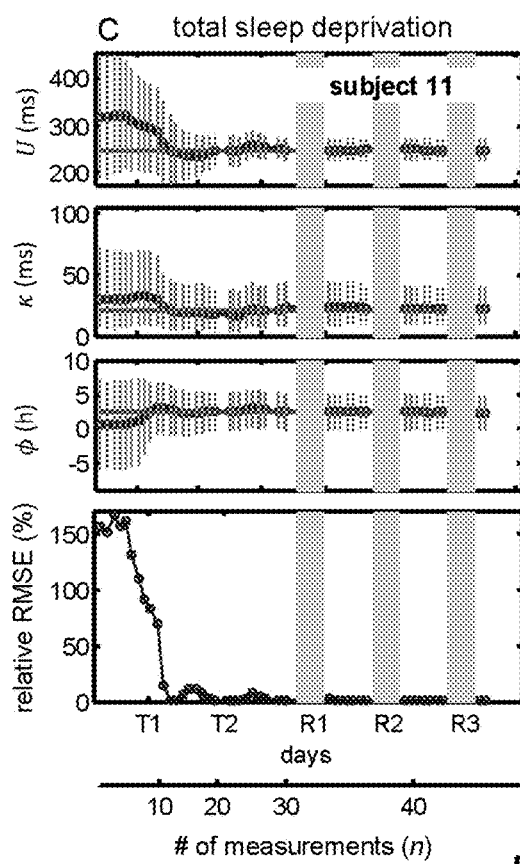
Figure 2D:
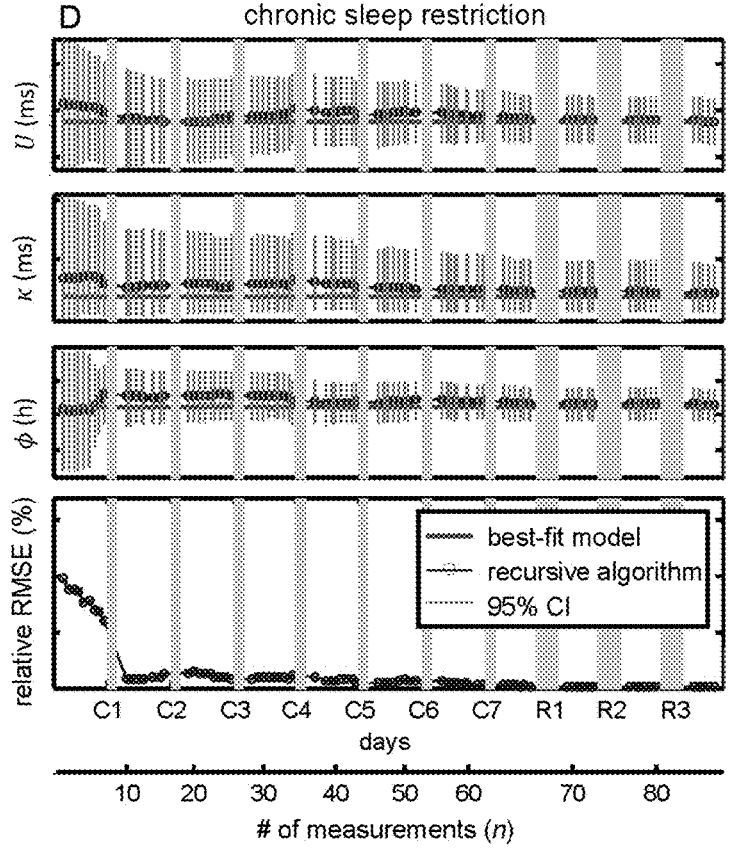

To assess the ability of the model to learn an individual's response to sleep loss with the recursive algorithm, its temporal convergence to the best-fit model was evaluated. FIGS. 1A-1D show the measured PVT performance data along with the results for the best-fit model, group-average model (whose parameters were used as the starting values (n=0) for the recursive algorithm), and recursive algorithm using the first n=15 and n=30 PVT measurements for the TSD challenge (FIGS. 1A and 1C) and the first n=30 and n=60 PVT measurements for the CSR challenge (FIGS. 1B and 1D). FIGS. 1A-1D show the results for two subjects: subject 2 in FIGS. 1A and 1B and subject 11 in FIGS. 1C and 1D. The two subjects demonstrate different patterns of response to sleep loss. For each subject and challenge, as the number of measurements n increased, the performance trajectories for the recursive algorithm became progressively closer to those of the best-fit model. For example, FIG. 1C shows that the model learned subject 11 using the recursive algorithm with n=30 almost as well as the best-fit model and considerably better than the n=15 model. Note that the recursive algorithm plots indicate the result of model fitting up to the first n measurements and model predictions thereafter. The group-average model consistently overestimated subject 11 and consistently underestimated subject 2, highlighting the inherent inability of group-average models to capture large inter-subject variability to sleep loss and the benefit of developing individualized models.

FIGS. 2A-2D show the corresponding values of the recursive algorithm estimates for the three most sensitive model parameters, U, $\kappa$, and $\phi$, their associated 95% confidence internals (CI), the best-fit model parameters (horizontal lines), and the relative RMSEs as a function of PVT measurements n. Although for n=1 some of the recursively estimated model parameters were far from the best-fit model parameters (e.g., U for subjects 2 and 11), as n increased, each of the parameters converged toward their respective counterparts of the best-fit models and the 95% CIs became progressively smaller. Compared with CSR, the 95% CIs of the parameters under TSD were consistently smaller at the end of the recursive learning period despite the smaller number of available measurements (51 vs. 85 measurements). For both subjects and across the two challenges, the relative RMSEs between the recursive algorithm and the best-fit model approached zero as n increased, indicating that the differences in the model outputs became increasingly smaller over the course of learning, as shown in FIGS. 1A-1D. The reduction in the relative RMSEs was significantly faster at the beginning of the learning process when large discrepancies between PVT data and recursive model outputs led to large parameter adjustments in Eq. (11). No significant reduction was observed in the relative RMSEs during the recovery phase (8 hours TIB in each of days R1, R2, and R3), suggesting that by that time the recursive algorithm had largely learned the subjects.

Figure 3A:
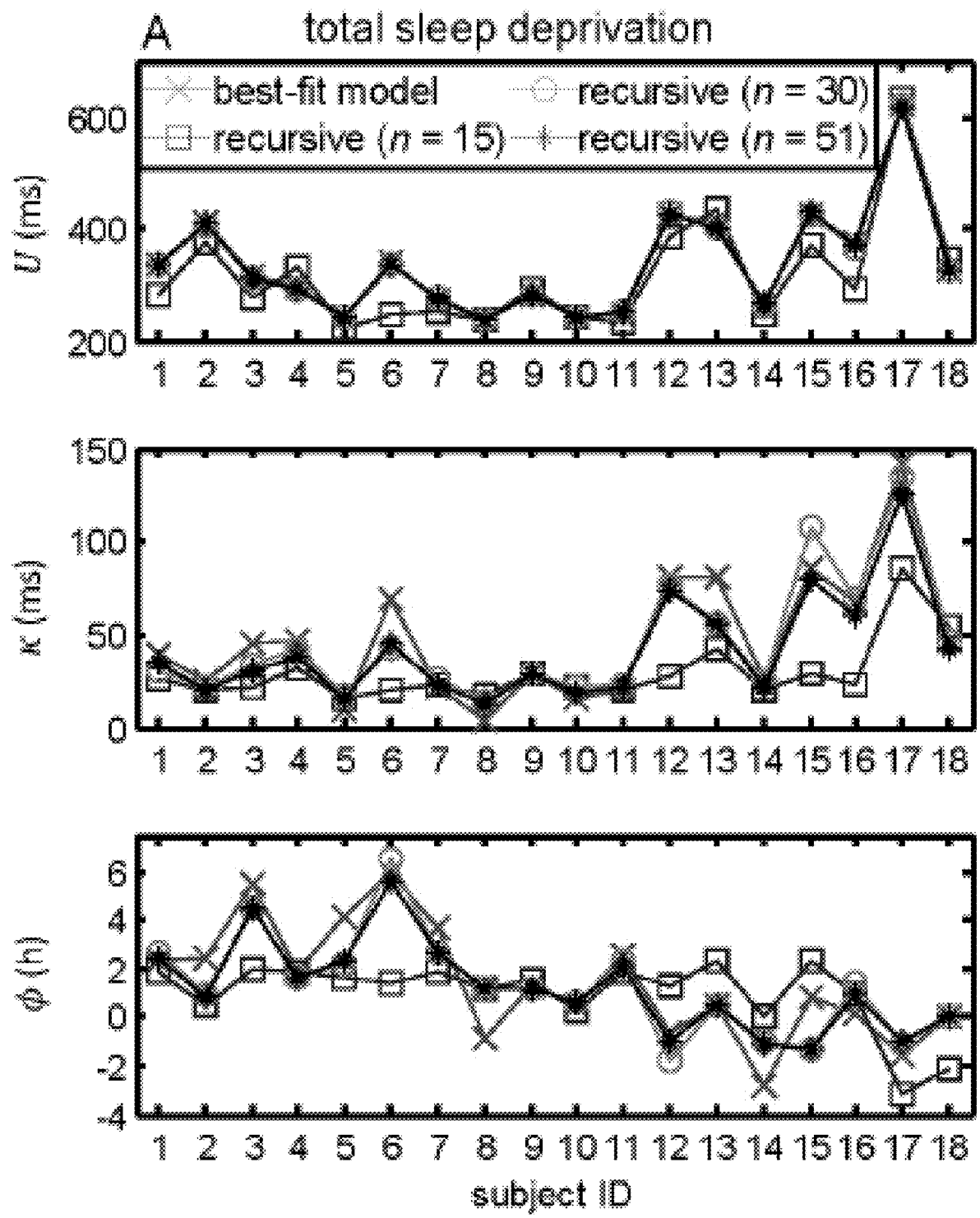
FIGS. 3A and 3B show the best-fit model estimates for three parameters for the test subjects along with the corresponding recursive algorithm estimates.
Figure 3B:
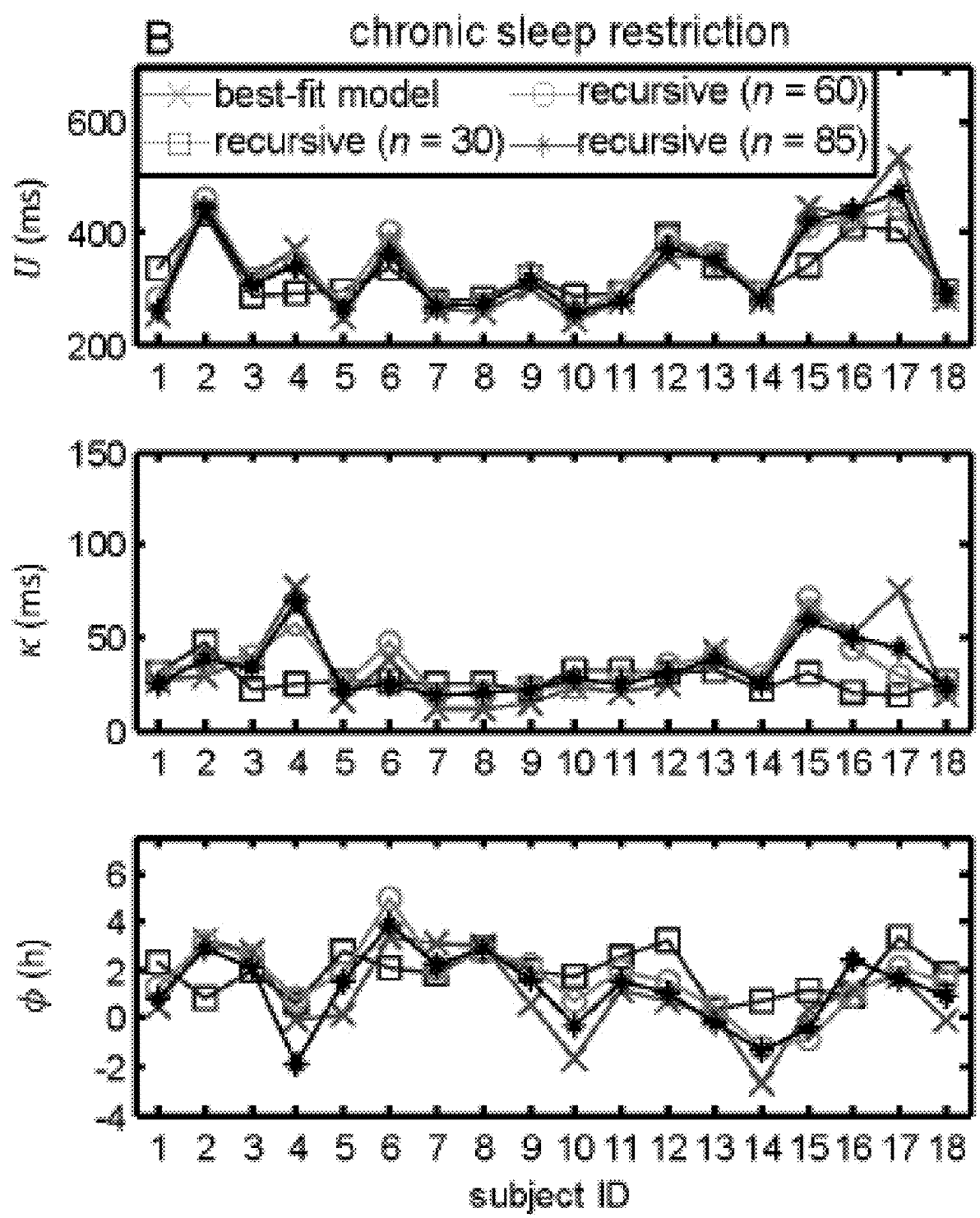

FIGS. 3A and 3B show the best-fit model estimates for parameters U, κ, and φ for each of the 18 subjects along with the corresponding recursive algorithm estimates after n=15, 30, and 51 measurements for TSD and after n=30, 60, and 85 measurements for CSR, respectively. For all subjects, as more PVT measurements became available, each of the recursively estimated parameters converged toward their respective counterparts of the best-fit model. For TSD, the recursive algorithm estimates generally converged to their final values (i.e., the values obtained using all n=51 measurements) after n=30 and, except for a few subjects for parameters κ and φ, these estimates also converged to those of the best-fit model. A similar trend for CSR occurred, although convergence required a larger number of training data points (n=60) and the convergence was not as tight as the TSD results, consistent with the results shown in FIGS. 2A-2D. Variability in the rate of parameter convergence among the different subjects was observed, which was likely caused by the similarity or lack thereof between the initial parameter values at n=0 (i.e., the group-average parameter values) and the best-fit model estimates for a subject.

f. Number of PVT Measurements Required to Learn an Individual

Figure 4A:
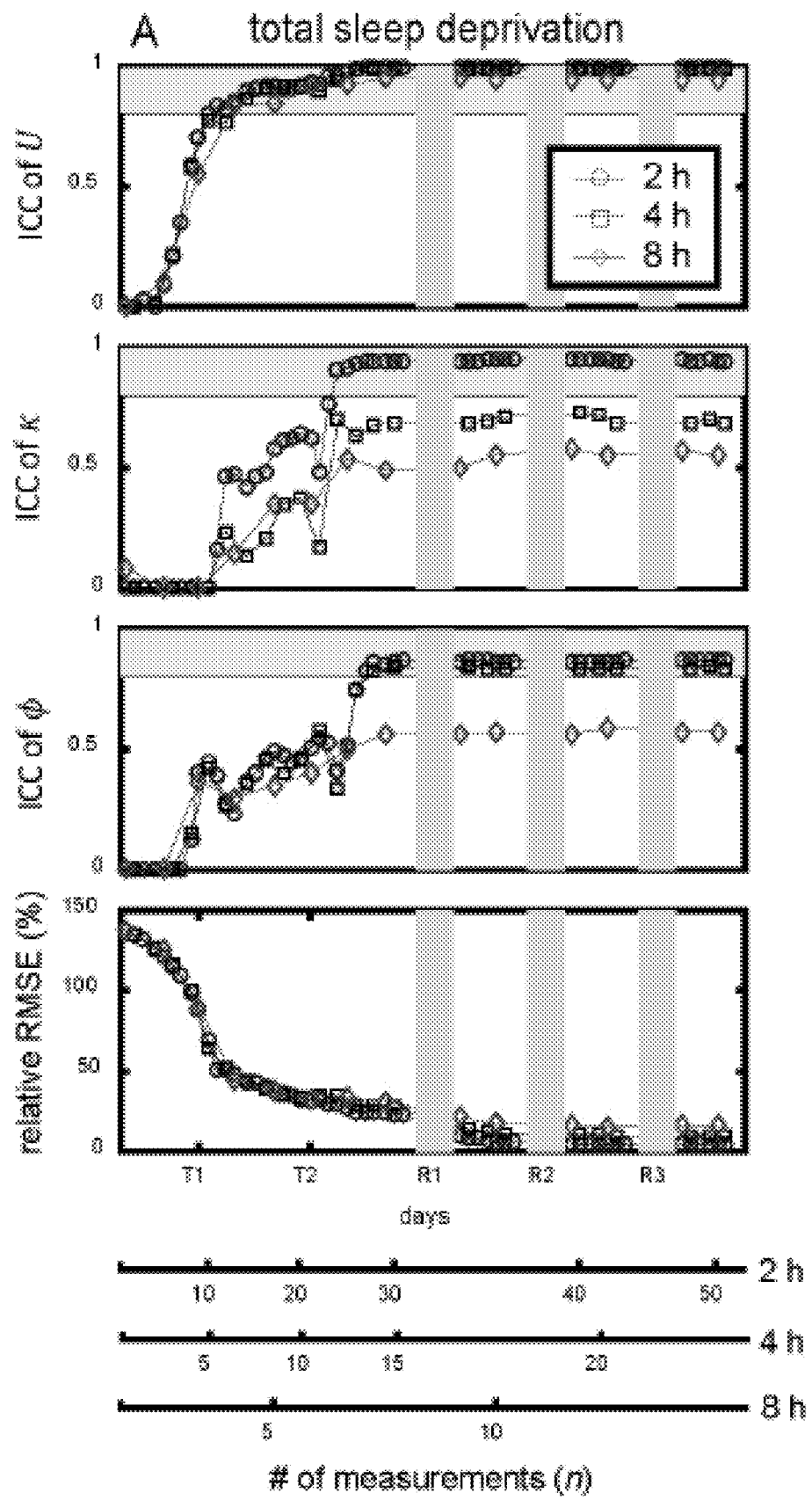
FIGS. 4A and 4B show data related to a total sleep deprivation and chronic sleep restriction study data with downsampling of PVT test frequency.
Figure 4B:
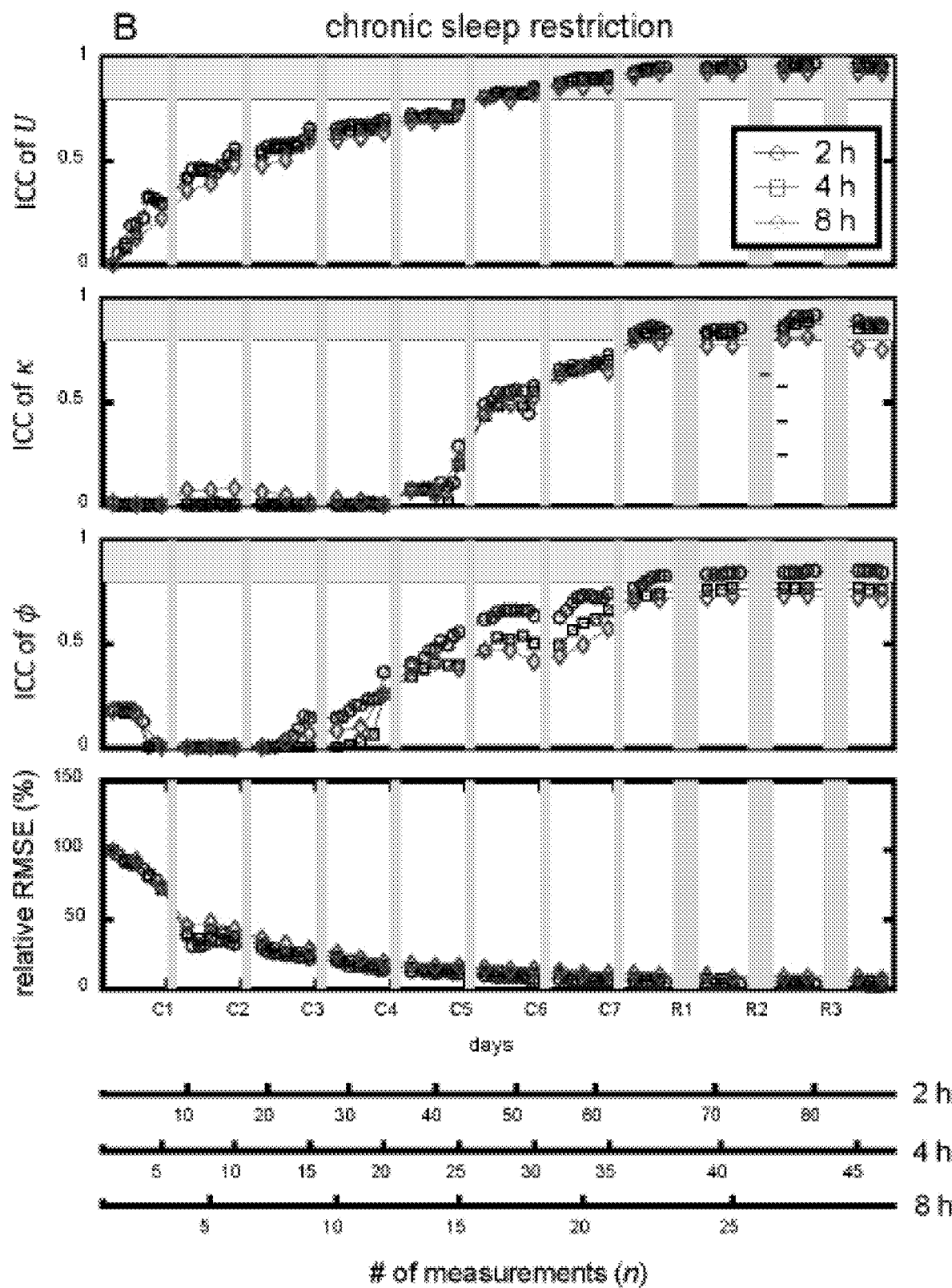

To globally quantify the algorithm's rate of learning of the 18 subjects' trait-like response to sleep loss, the intraclass correlation coefficients (ICC) of the parameter estimates were computed between those of the recursive algorithm and the best-fit model as a function of the number of PVT measurements (FIGS. 4A and 4B). For TSD (FIG. 4A), the recursive algorithm required n=25 PVT measurements sampled every 2 hours for the ICCs of each of the three parameters, U, κ, and φ, to exceed 0.80 (which indicates an almost perfect agreement, i.e., parameter convergence); for CSR (FIG. 4B), it required n=62 measurements sampled every 2 hours during wakefulness. Significant differences are observable in the rate of learning of the different parameters. For both challenges, U reached an almost perfect agreement considerably earlier (n=10 for TSD and n=44 for CSR) than the two other parameters. In fact, the recursive algorithm estimates of the circadian amplitude κ and circadian phase φ did not start to converge towards the best-fit model until after n=10 (~19 hours) under TSD and after n>20 (~53 hours) under CSR.

To globally quantify the convergence of the model outputs as a function of PVT measurements, the average relative RMSE was computed between the recursive algorithm and the best-fit model over the 18 subjects as illustrated in the bottom graph of FIGS. 4A and 4B. For TSD, the recursive algorithm required n=32 measurements sampled every 2 hours to yield a relative RMSE of <10% (an arbitrary definition of model output convergence, which corresponds to ~5 ms for mean RT under TSD). For CSR, it required n=44 sampled every 2 hours during wakefulness. Hence, under TSD, the model outputs converged approximately when the estimated recursive algorithm parameters converged (n=25), however, under CSR, the model outputs converged considerably before (n=44) the parameters attained full convergence (n=62). Besides the arbitrariness in the definitions of convergence, two other reasons may have contributed to this apparent inconsistency in the discussed model. First, the convergence of model outputs is strongly driven by the convergence of the most sensitive model parameter (the parameter U). Second, different combinations of the less sensitive model parameter values (e.g., κ and φ) can yield equivalent model outputs.

g. Impact of PVT Measurement Frequency on Model Individualization

The above-described analyses used PVT data measured every 2 hours throughout wakefulness. Accordingly, to assess the impact of PVT measurement frequency on the rate of model individualization with the recursive algorithm, the data was downsampled by a factor of 2 to simulate 4-hour sampling and by a factor of 4 to simulate 8-hour sampling and computed the ICCs and average relative RMSEs as a function of the number of measurements as illustrated in FIGS. 4A and 4B. Reducing the frequency of PVT measurements from once every 2 hours to once every 4 hours did not significantly affect the learning rate of the model parameters, except for the ICC of the circadian amplitude κ under TSD and for the ICC of the circadian phase φ under CSR, which only reached levels of substantial agreement (0.61<ICC<0.80). However, because U was the main driver of the model outputs and its learning seemed to be insensitive to sampling frequency, downsampling from 2 to 4 hours did not significantly affect the relative RMSE. In contrast, we observed that a further reduction in measurement frequency to once every 8 hours had a more pronounced effect on the learning of the circadian rhythm parameters and, to a less extent, on the model outputs, which was more noticeable for TSD. Based on the above, in at least one embodiment the PVT tests occur 4 or 5 times a day during waking hours (e.g., about every 4 hours if a PVT test is done shortly after awakening) for about a week. In an alternative embodiment, the test frequency can be different.

Applications for predicting an individual's neurobehavioral performance using a mobile computing platform in at least one embodiment are individualizable, and thus capable of automatically "learning" the individual's trait-like response to sleep loss over time. To this end, a process for individualizing the model of performance in real time is provided by at least one embodiment. In this discussed embodiment, individualization is achieved recursively, in a computationally efficient manner, by updating the model parameters solely on the basis of the individual's most recent response-time measurements via an algebraic equation.

Overall, a practical implication of these findings is that, for the purpose of individualizing the model, 4-hour PVT sampling results in minimal decrements in model performance when compared to the more demanding 2-hour sampling schedule that has been commonly used in laboratory studies, and data collection periods spanning longer durations (a desirable attribute in operational environments) improve the learning ability of the recursive algorithm.

One of the limitations of this study is that the results are based on a crossover-design laboratory study involving 18 healthy young adults who underwent 64 hours of TSD and 7 days of CSR of 3 hours nightly TIB. Moreover, because CSR challenges can vary in both length and severity, it is not clear to what extent the insights gained in the CSR analyses are generalizable to other challenges, especially less severe CSR schedules. To address this limitation, the simulations were repeated for another CSR study, in which different subjects were challenged with 7 consecutive nights of 3, 5, 7, or 9 hours of TIB per night. The results suggest that, while it took considerably longer to learn the subjects in the 9-hour TIB group, the recursive algorithm progressively learned the subjects in the 3-, 5- and 7-hour groups after about 1 week of 6, 5, and 4 PVT measurements/day, respectively. Moreover, because TSD represents the upper limit of CSR, its results provide a lower bound to the findings. Another limitation is that the results are based on PVT test statistics. The recursive algorithm provides an approximate solution to a nonlinear optimization problem. Nevertheless, the present results provide evidence that such an approximation is adequate for identifying model parameters, because the recursive algorithm results converged to those obtained by exactly solving the nonlinear optimization problem.

In summary, the above demonstrates the ability of a recursive algorithm to individualize the model parameters in real time in a computationally efficient manner.

h. System Embodiments

Figure 5A:
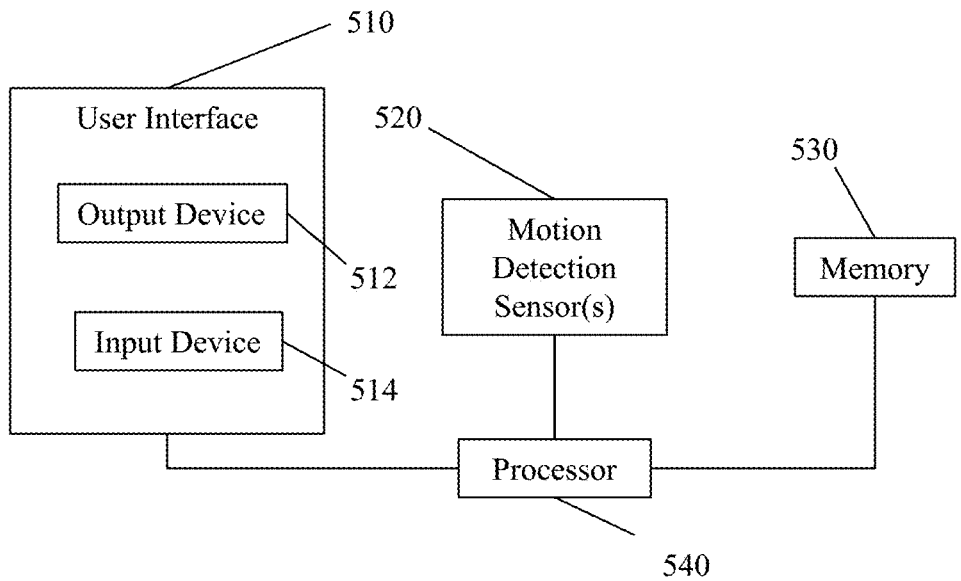
FIGS. 5A and 5B illustrate block diagrams of at least two system embodiments according to the invention.

The system in at least one embodiment includes a computing device (or system) that includes a user interface 510, a motion detection sensor(s) 520, a memory 530 and a processor 540 as illustrated in FIG. 5A. Examples of a computing device include a wrist-worn device, a smart phone, a tablet and/or any combination of these. In an alternative embodiment, the worn device is located on a different body part. Examples of wrist-worn devices include commercially available activity monitors, such as those devices sold by Fitbit®, Apple®, Samsung®, and Garmin®. In at least one embodiment, it is the combination of multiple separate components, such as a wrist-worn device having the motion detection sensor(s) 520 and communicating with an optional computing device, such as a smart phone, a tablet or a computer (laptop or desktop), that would have the user interface 510, the memory 530 and the processor 540 where the wrist-worn device would be capable of communication with the computing device. Although in alternative embodiments, other combinations of components between the wrist-worn device and the computing device. In such an embodiment, the devices would communicate using a wireless protocol, such as Bluetooth® or WiFi or via a wired connection. As such, the components in at least one embodiment are present at least partially within a housing.

In at least one embodiment, the user interface 510 includes at least one output device 512 with functionality to provide information to the user via visual, sound, mechanical, and/or any combination of these. Examples of the output device 512 include a display(s) (or touchscreen), at least one light, a speaker, and a transducer. In at least one embodiment, the user interface includes at least one input device 514 with functionality to receive input from the user such as sleep information, caffeine consumption and/or responses during a PVT test. Examples of the input device 514 include a touchscreen(s), a button(s), a switch(s), a touchpad(s), a keyboard, an external accessory, a communications module, and/or a microphone. In at least one embodiment, the examples of the input device 514 are examples for a receiving means for receiving input from the user.

In at least one embodiment that allows for individualization, the user interface 510 facilitates the giving of the PVT test to the user and receiving the user's response, such as through a touchscreen or a light and button pair/combination. In a further embodiment, the user requests the start of a PVT test at a time convenient for the user as opposed to a time determined by the system such as would occur based on a test schedule (i.e., at 2, 4, 6, or 8 hour increments during non-sleep), an open period of time on the user's schedule as obtained from the user's calendar that resides on the computing device, or a level of user activity being indicative of sitting. In a further embodiment, informing the user of an upcoming PVT test through the user interface 510 such that the user may decline and/or postpone the PVT test until a more convenient time such as through a "snooze" option or setting of a future time.

In at least one embodiment, the computing device includes at least one motion detection sensor 520 to track user activity and/or movement. Examples of such sensors 520 include an actigraph and/or an accelerometer. The sensor 520 in at least one embodiment allows for the computing device to determine whether the user is asleep or awake to facilitate the development of a sleep history for the person. In an alternative embodiment, the motion detection sensor 520 is omitted and the sleep history is provided via the user interface or a data file for use in the model. In an alternative embodiment, the sensor 520 is present, but it is possible to edit the recorded sleep history and/or enter retrospective/predictive sleep history information.

In at least one embodiment, the memory 530 stores the data produced by the motion detection sensor 520 or alternatively provided by the user or another individual and any information that the user provides. In at least one embodiment, the data is stored in a database residing in the memory 530. The memory 530 also stores the model and the parameter weights for the model including any default weights for an average individual, which can serve as a default, and/or the individualized weights for the user. In at least one embodiment, the memory 530 stores the executable code for the processor 540 to perform the described methods in this disclosure.

In at least one embodiment, the processor 540 is in electrical communication with the memory 530 and is capable of communication (directly or indirectly depending upon the particular implementation) with the user interface 510 and the motion detection sensor 520. The processor 540 is configured to run the executable code to perform the described methods. In at least one embodiment, the processor 540 is configured to drive the user interface 510.

In at least one alternative embodiment, the processor 540 initiates a PVT test in response to the user notifying the system that he/she is about to consume caffeine or has just consumed caffeine and then is scheduled to run a second PVT test approximate the time the caffeine is scheduled to have been metabolized and/or at least one point in time from the current time to the metabolized time. With the PVT test results being used to adjust the caffeine related parameters in the model. This PVT test set would be in addition or in place of other PVT tests although in at least one embodiment, a PVT test scheduled during this would be skipped.

In at least one embodiment, the system further includes a power source (not illustrated), such as a battery or other source, to provide electrical current to the system components.

Figure 5B:
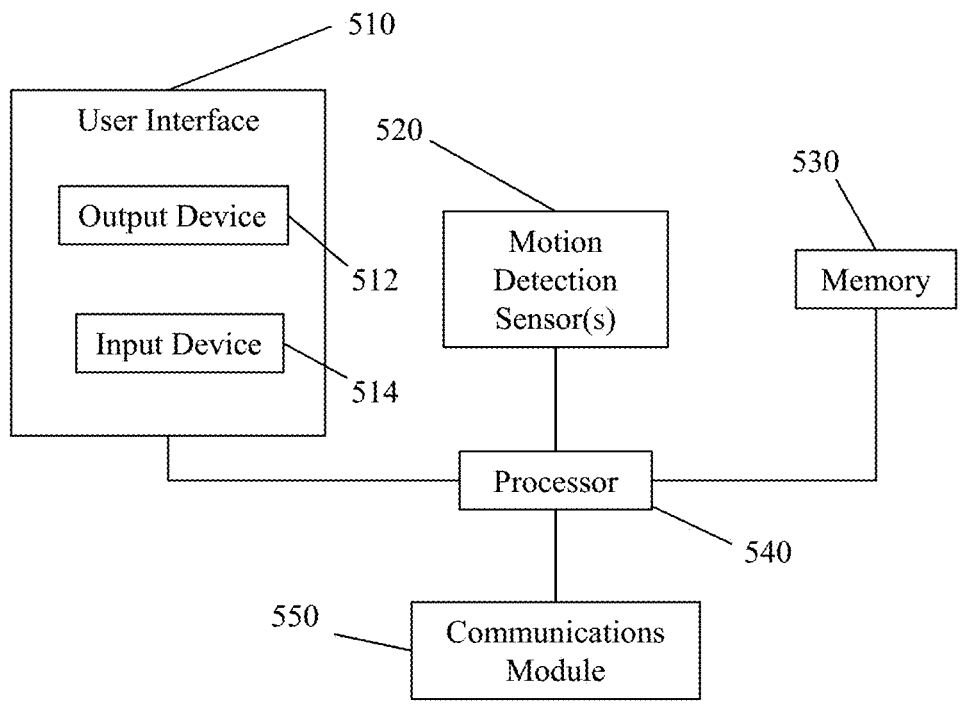

The system in a further embodiment to the above system embodiments may include an optional communications module 550 as illustrated in FIG. 5B. In at least one embodiment, the communications module 550 includes the ability to communicate with an external device. Examples of a communications module 550 include, but are not limited to, a transmitter, an antenna, a receiver, a transreceiver, a light source, a light sensor, and a plug (or other connector) configured to receive a wire connection. In at least one embodiment, the communications module 550 facilitates communication between a smart phone, tablet, or a computer with a wrist-worn device or a networked server as discussed later in this disclosure.

Figure 6:
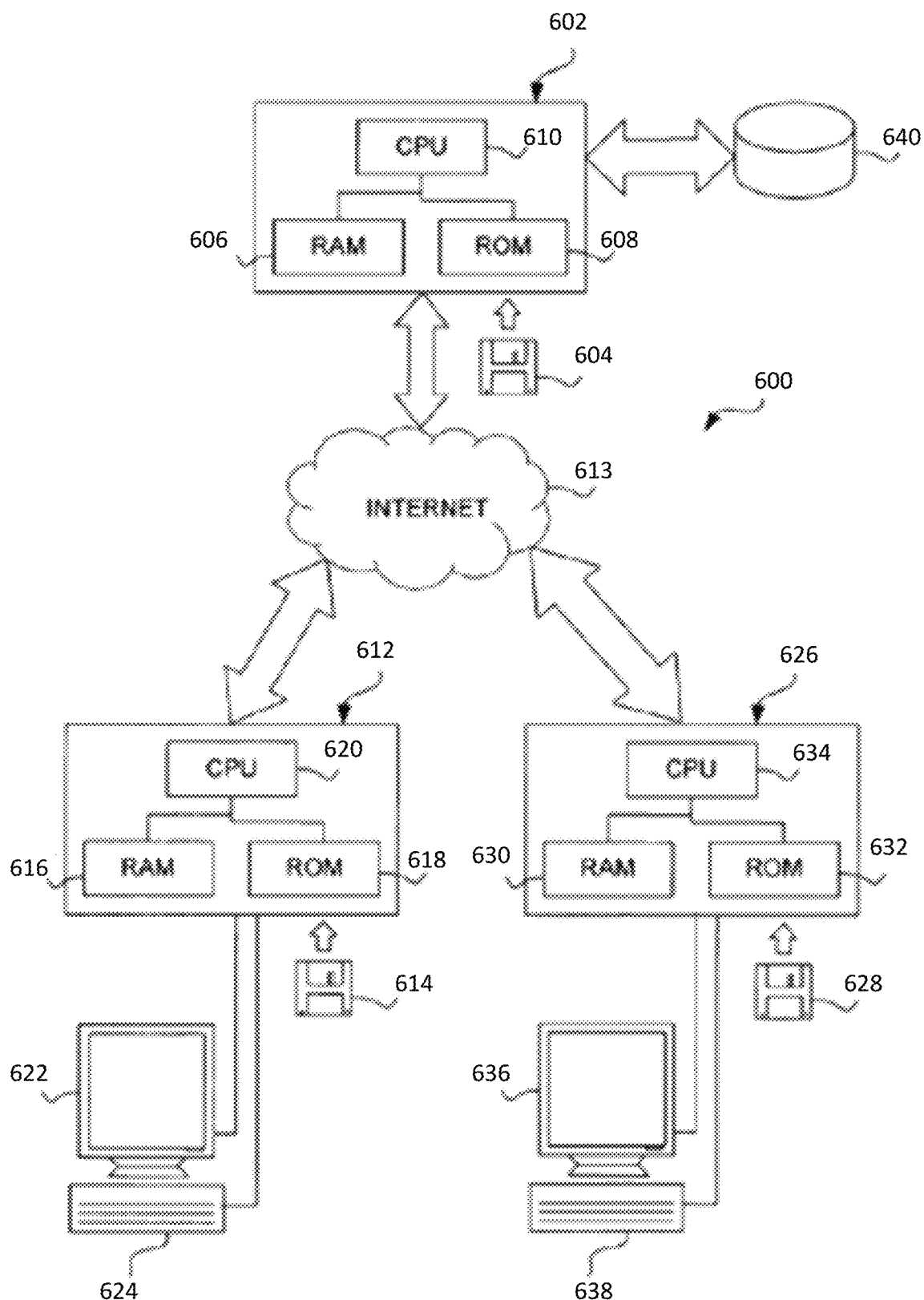
FIG. 6 is a pictorial block diagram of a network embodiment of the invention.

In at least one embodiment illustrated in FIG. 6, a computer network 600 is configured for providing prediction support to one or more individuals. Such an embodiment would be advantageous in scheduling a workforce or locating a replacement individual using current cognitive state for individuals that make up the workforce. The computer network 600 is useful in many varied contexts in which statistical regression models can be used to predict outcomes. To provide decision support, some embodiments are configured to generate outputs, including graphical outputs and patient reports that incorporate such outputs.

In some configurations, computer network 600 includes a server computer 602 that executes a server module. The server module includes software instructions recorded on a machine-readable medium or media 604. Machine-readable medium or media may compromise, for example, one or more floppy diskette's, CD-ROMs, CD-RWs, DVDs, DVD-Rs, DVD-RWs, memory devices such a USB memory sticks or other types of memory cards, internal readable and writable memory 606 of any of various kinds, such as internal or external RAM, read only memory (ROM) 608 of any of various kinds, hard disks optical drives, and combinations thereof, but it does not include transitory signals. As used herein, "media" includes not only "removable" media, but also "non-removable" media such as primary and secondary storage. For example, RAM, ROM, and hard disk drives are included as "media," as well as the aforementioned types of media. Server computer 602 can include devices for reading removable media, such as CD-ROM drives, a DVD drive, a floppy disk drive, etc. In many configurations, server computer 602 will include at least a readable and writable memory 606, read-only memory 608 or non-volatile memory of a suitable type, and a processor 610 (e.g., a central processing unit or CPU) which may itself include one or more microprocessor, co-processors, etc. Thus, the term, "processor," as used herein, is not literally restricted to a single CPU. Moreover, server computer 602 may itself include a network of one or more computers, as can any other device referred to as a "computer" herein.

Computer network 600 further includes one or more first client computers (or portable computing devices) 612, such as illustrated in FIGS. 5A and 5B. In many configurations, it is in communication with the server computer 602 via a network 613, for example, the Internet or LAN. In at least one embodiment, the client computer 612 includes a first client module including software instructions recorded on the machine-readable medium or media 614. In many configurations, client computer 612 further includes at least a readable and writable memory 616, read-only memory 618, and a processor 620 that may itself include one or more microprocessors, coprocessors, etc. First client computer 612 may itself include one or more computers in a network. First client computer 612 further may include a first user display device 622, such as a CRT display, LCD display, plasma display, and/or a hardcopy device such as a printer. First client computer 612 may also include a first user input device 624, such as a keyboard, a mouse, a touchscreen (which may be part of the display 622), and/or a trackball, etc. First client computer 612 is not limited to desktop or laptop computers that can include any computing device that can communicate over a network. For example, in some configurations, a first client computer 612 can be a digital assistant (PDA) or a wireless telephone with a display screen, or other "smart phone" type devices.

Computer network 600 further includes one or more second client computers 626. In at least one embodiment, second client computer 626 is in communication with server computer 602 via network 613. In at least one alternative embodiment, second client computer 626 includes a second client module having software instructions recorded on a machine-readable medium or media 628. In many configurations, second client computer 626 further includes at least a readable and writable memory 630, read-only memory 632, and a processor 634 that may itself include one or more microprocessors, coprocessors, etc. Second client computer 626 may itself include one or more computers in a network. Second client computer 626 further includes a second user display device 636, such as a CRT display, LCD display, plasma display, and/or a hardcopy device such as a printer. Second client computer 626 also includes a second user input device 638, such as a keyboard, a mouse, a touchscreen (which may be part of the display 636), and/or a trackball, etc.

As used herein, software instructions "instruct the computer to display" information even if such information is communicated via a network to another computer for display on a remote display terminal. In this sense, code running on a web server instructs a processor executing that code to "display" a webpage, even though the code actually instructs the processor to communicate data via a network that allows a browser program to instruct in other computer to construct the display of the webpage on the display of the other computer. For example, the server module described in the examples presented herein can include a web server and the client modules can comprise web browsers. Also, in some configurations, client computers 612 and 626 include laptop, desktop, or mobile computing devices or communication terminals. The broader scope of the phrase "instruct the computer to display" is used because server computer 602 and the one or more client computers 612, 626 need not necessarily be different computers. For example, communication protocols known in the art allows server software module and a client software module running on multitasking computer systems to communicate with one another on the same computer system, and the same server software module can also communicate with a client software module running on a different computer via a network connection.

The terms "display" and "accept" as used in the description herein referred to a suitably programmed computing apparatus "displaying" or "accepting" data, not to a person "displaying" or "accepting" something. A person might, however, view the display data on an output device on a page produced by an output device or supply the accepted data using an input device.

In at least one embodiment, a method provides decision support via software that operates on the server module. At least one embodiment includes server modules that utilize that ASP.NET platform available from Microsoft Corporation, Redmond, Wash. as well as and as Internet information services (IIS) and Microsoft® SQL server from Microsoft® Corporation for Web services and data storage, respectively.

A multitier system architecture in at least one embodiment enables scaling of server module components as needed to meet specific demands of a particular deployment. In addition a modular design framework is used in at least one further embodiment to facilitate extensibility and incorporation of new functionality via custom modules. In at least one embodiment, the server module is written in C++ or C#; except for its SQL data access components which are stored procedures written in SQL. The described embodiments are not limited to implementation using the tools described above. For example, at least one embodiment can run on the LINUX® operating system and be built using a different suite of applications. The selection of an appropriate operating system and suite of applications can be left as a design choice to one of ordinary skill in the art after such person gains an understanding of the present disclosure.

The technical effect of at least one embodiment is achieved first by user logging in with the appropriate credentials. Server module instructs processor 610 to display a visual selection of input parameters, for example, on a user display device 622. An example of such interface is illustrated in FIGS. 7 through 23 and may include a Graphical User Interface (GUI). In some embodiments, access to these features is available only to those with administrative rights. In some embodiments, the GUI includes standard GUI elements such as windows, dialog boxes, menus, drop-down lists, radio-buttons, check boxes, icons, etc.; and the module provides functionality to define and express parameter input and output display options, such as mouse movements and mouse clicks. User interaction with the interface is achieved by one or more methods that may include, for example, pointing and clicking with the mouse, touchpad, or other input device, or typing on a keyboard, or speaking into a microphone and using voice command recognition software. In some embodiments, models, normative data, parameter inputs, display options, etc. (comprehensively referenced herein as Data) are imported, either in part or in their entirety, from all-text representations, examples of which include, but are not limited to, XML-based documents. Some embodiments allow imported Data to be edited and modified, stored in a memory of the server computer or elsewhere, and/or re-exported in their original formats and/or other formats.

A general regression model framework is used in at least one embodiment for expressing predictions. The model types can include, for example, linear, generalized linear, cumulative multinomial, generalized multinomial and proportional hazard models. Model types may be defined in terms of a coefficient vector and an optimal covariance matrix for calculating confidence intervals.

In at least one embodiment, the request for model parameters is sent via an XML Web service for programmatic access. In configurations in which the request is sent via an XML Web service, the request is not necessarily "displayed" as such.

In at least one embodiment, coefficient values (or variable weights) are obtained by instructions to processor 610 to run a regression analysis on data obtained from a database 640, which may be a local database stored in server computer 602 or a database accessible via network such as network 613. A list including the outcome, associated coefficients and accepted names, types, and/or limits for variables are stored in a memory (e.g., memory 606, a secondary storage unit, or even a register of the processor) of server computer 602 for later use at step. The term "later use" is intended to be interpreted broadly and can include, for example, use as part of the running of a stored model at a later date, use as part of a self-contained PDA version of the application, or use by a non-registered user who approached the application through the web to do a "one-off" run of a model. At least one embodiment also updates weights and covariance matrices that are stored for the model.

Referring back to FIG. 6, at least one server module also contains instructions configured to instruct processor 610 to allow a user (usually, but not necessarily different from the user at first client computer 612) at second client computer 626 to log into the server module. The user at second client computer 626 is able select one or more of the stored regression model specifications, input data for the stored models, run a regression analysis that can be presented with results of the regression analysis are analyses.

Figures 15, 16, 17, 18:
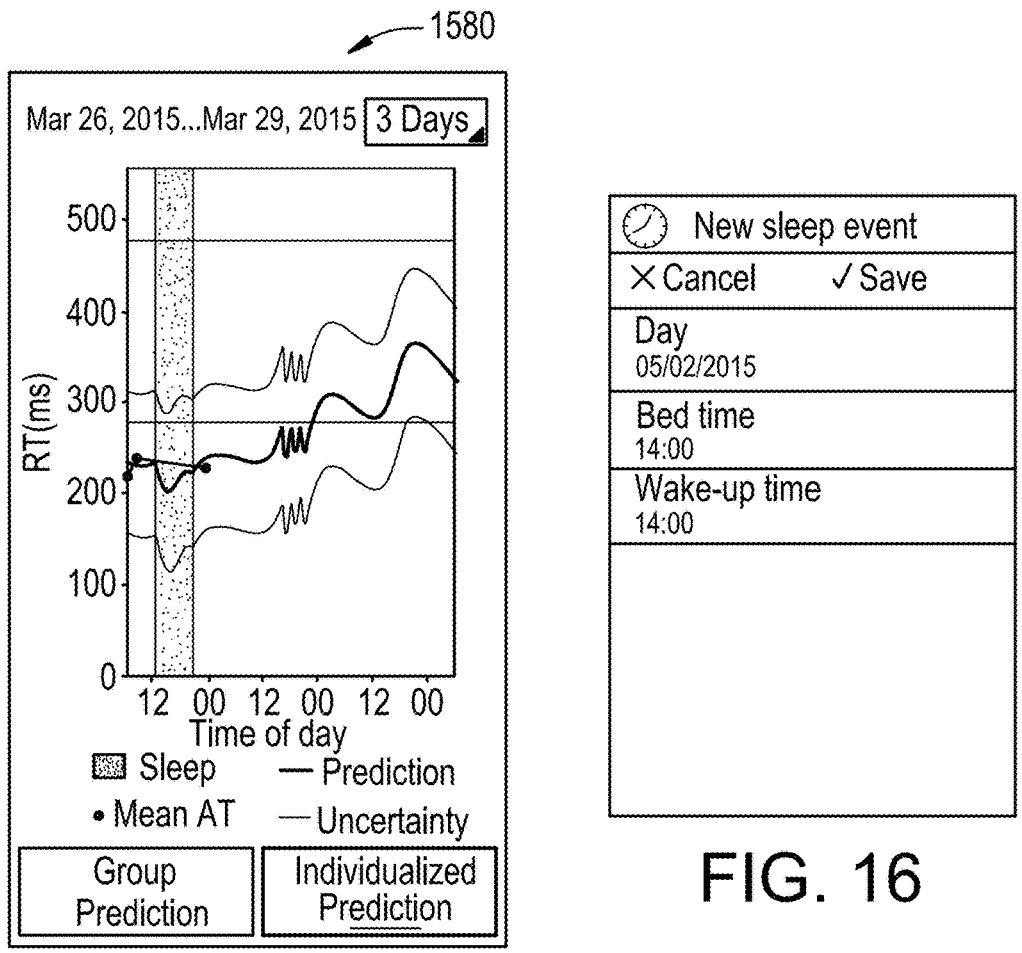
FIG. 15 illustrates a graphical user interface display relaying the results of a prediction of cognitive performance using individual statistics after an interval of sleep.
FIG. 16 illustrates a graphical user interface display relaying a user sleep log.
FIG. 17 illustrates a graphical user interface display relaying a date input interface.
FIG. 18 illustrates a graphical user interface display relaying a time input interface.

The server module accepts the collected Data (which may also include an identification of a person or object to which the variables apply) and runs the selected regression model specifications. The results of the selected regression model specifications are displayed. An example of such a display is illustrated in FIGS. 13-15. The displayed results can also include a representation of a statistical range, such as a visual representation in some illustrated embodiments. Also in some illustrated embodiments, and referring again to FIG. 19, processor 610 is instructed to use customizable content previously stored in a memory or database accessible to processor 610 and optionally including return addresses, logos etc. to print the results or to cause the results to be printed.

Main effects and interaction terms derived from input parameters and their transformations can be derived in some embodiments, and regression coefficients for calculating point estimates for outcome of interest and optional covariance estimates can be provided for computing confidence intervals.

Figure 25:
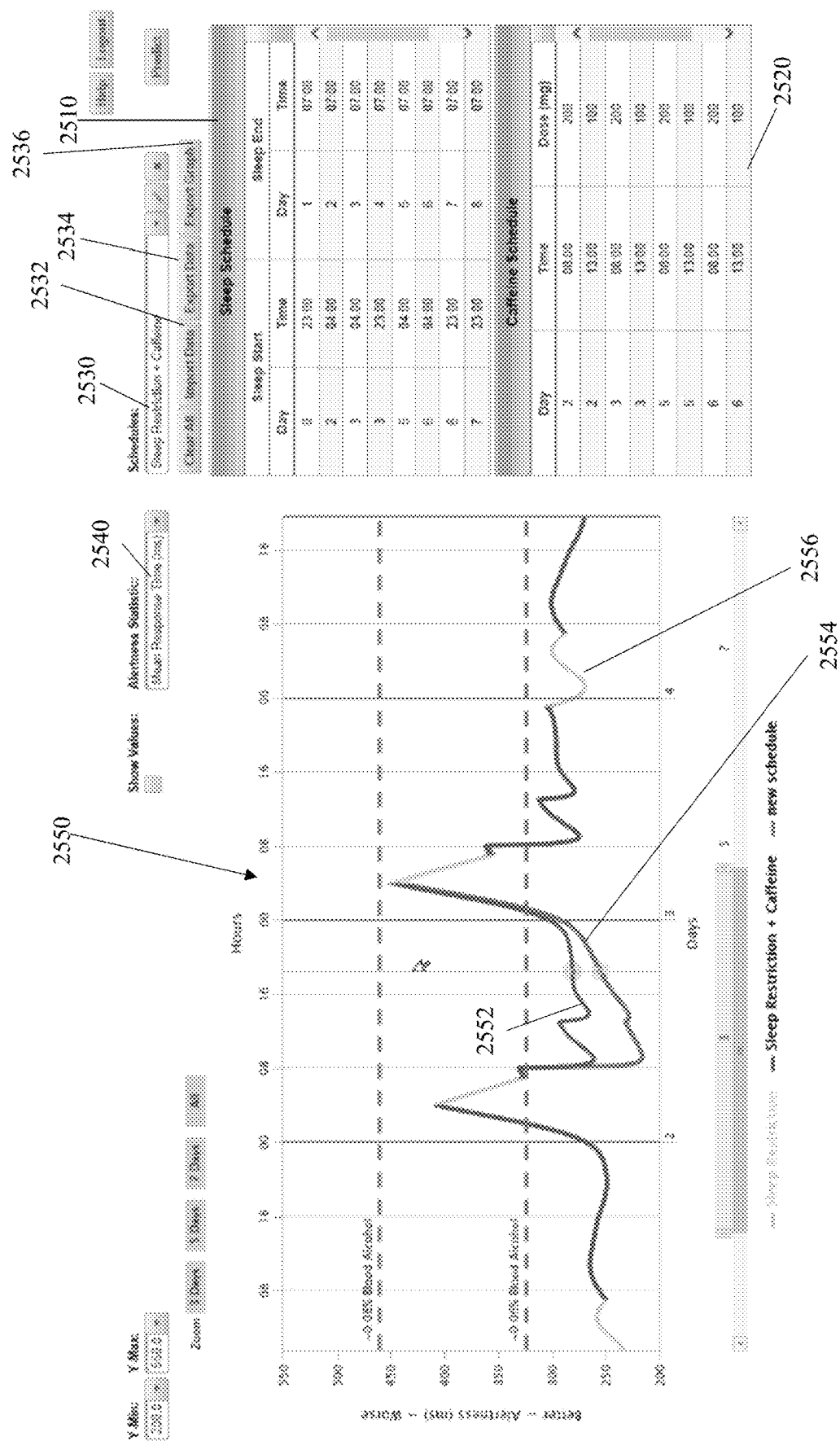
FIGS. 25 and 26 illustrate different user interfaces for interacting with at least one server embodiment according to the invention.
Figure 26:
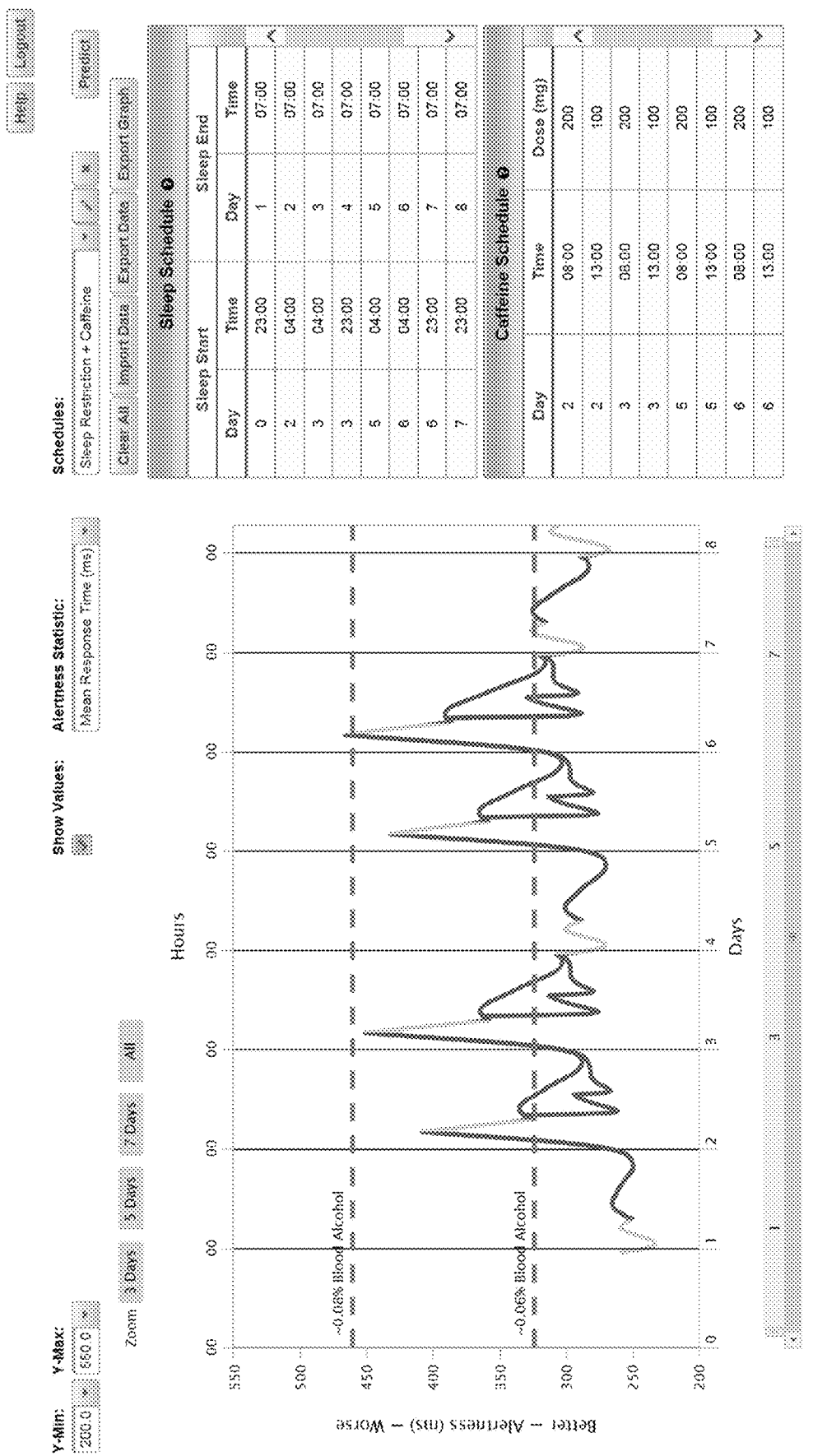

Healthcare providers (or, in other environments, other individuals) can readily access regression model specifications through an integrated and customizable portal interface using a variety of web-enabled devices, such as that illustrated in FIGS. 25 and 26. Dynamically generated data and free screens are provided based on the variables required by the selected models.

In at least one embodiment, model outputs are rendered in a variety of graphical and non-graphical formats, including solid bar plots, gradient bar plots, whisker line plots, high charts, and/or digital LED-style displays, which can be user-selectable. Output from multiple models can be grouped onto a single plot to facilitate inter-model comparison, see, e.g., FIGS. 25 and 26. At least one embodiment allows a user to customize the output plot style, the selection of models to include a final output and the display of confidence intervals (when model covariance data has been provided), see, e.g., FIGS. 13-15. In at least one embodiment, users can print outcome plots using customizable report templates in order to generate documents such as educational materials and informed consent sheets. In at least one embodiment, outcomes researchers can customize report and page content using a built-in word processor-like interface or by editing HTML code. A feature-rich set of portal content modules, including work-group directories, discussion threads, and document repositories may be provided in as part of a server module to allow outcomes research groups to easily create, manage, and build their own collaborative websites.

It will thus be appreciated that at least one embodiment can be used to handle various aspects of data collection, validation, storage/retrieval, and processing, thereby freeing 1) outcomes researchers from intricacies of programming and networking and 2) supervisors/managers from reviewing data logs, asking individuals, or observing individuals to obtain information regarding cognitive state and/or alertness.

While the invention has been described in terms of various specific embodiments, those skilled in the art will recognize that the invention can be practiced with modifications within the spirit and scope of the claims.

Those skilled in the art should appreciate that storage units may illustratively represent the same storage memory and/or one or a combination of storage unit and computer memory within a computer system. Instructions that perform the operations discussed above may be stored in storage media or computer memory structures may be retrieved and executed by a processor. Some examples and instructions include software, program code, and firmware. Some examples of storage media include memory devices, tapes, disks, integrated circuits, and servers. Instructions are operational and executed by a processor to direct the processor to operate in accord with the invention.

Figure 24:
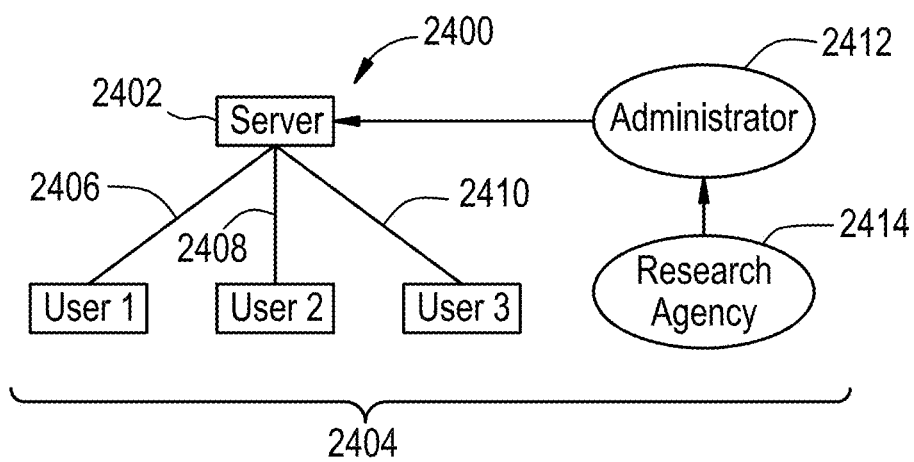
FIG. 24 illustrates a block diagram regarding another system embodiment according to the invention.

FIG. 24 illustrates a Wide Area Network (WAN) or Local Area Network (LAN) such as an intranet or the Internet, represented as system 2400 that may be configured with program instructions and data to implement the foregoing instrumentalities. Internet system 2400 may, for example, be a proprietary LAN or a WAN. Server 2402 is connected with a plurality of users 2404 or able to access the server 2402 for statistical processing of information. Connections 2406, 2408, and 2410 may be any type of data connection including wireless connection, coaxial connection, optical connection, Internet connection, or other type of connection across any geographic area. The Internet system 2400 may be implemented, for example 1) in a local hospital or in a plurality of local hospitals and 2) work locations across the city, estate, end nation, or countries throughout the world. In the illustrated embodiment, the users 2404 are each provided with suitable electronic equipment for establishing these connections, such as personal computers or PDAs. In at least one embodiment, this equipment is adapted for compatibility with other extant systems, such as billing systems, patient information systems, emergency response systems, and barcoding identification and tracking systems for patients end materials.

The server 2402 may, for example, store group data and/or may provide back-up storage for individual medical evaluation systems, as discussed above. Additionally server 2402 may provide a local agent or translator for plurality of individual medical evaluation systems to exchange information.

In at least one embodiment, the server 2402 provides centralized control under the supervision of an administrator 2412. The program instructions configuring server 2402 for use towards these ends are capable of accepting new models for different purposes, where these models are provided by the research agency 2414. In this matter, the research agency is able to provide updates to existing models that have been revalidated and/or expanded by comparing outcomes and demographics to survey responses. Additionally, the research agency may provide new models that may be selected by users 2404 to meet a particular need in the intended environment of use.

The system in an alternative embodiment further includes an interface for a research agency 2414 communicating with server 2402 and providing the statistical models using of visual interface communicated by server 2402. Server 2402 is configured to analyze requests received from users 2404 over the Internet, and intranet, or another network that relates to a plurality of statistical models and to reduce redundancy requests for patient data. Also, in some configurations, the statistical processing system further includes server 2402 operatively configured to present medical information questions to a user 2404 for human response and for receiving human responses to the medical information questions.

Based on the following description and FIGS. 7-23, one of ordinary skill in the art should appreciate that the illustrated GUIs could be modified for different display sizes and layouts. In particular, any color choices discussed could be changed in alternative embodiments.

Turning now to FIG. 7, at least one embodiment includes a GUI home page that allows a user to access various system functionality from one input interface. In the case of FIG. 7, the user may enter their sleep and caffeine dosing schedule, conduct a PVT session to train the individual model or assess current levels of alertness and cognitive performance, retrieve current information on the alertness status of the user and predict alertness status based no user inputs. The home-page also includes access to the system administrative and operations settings. It is understood that the options displayed in FIG. 7 are illustrative and that other embodiments could well include additional functionality.

FIG. 8 illustrates the graphical status guide 810 that informs a user of their current level of alertness/cognitive performance levels. A slider 820 is provided to allow the user to easily access the level of cognitive performance over time both going backwards as well as forwards in time. In at least one embodiment, when reviewing future levels, the processor may develop a projected sleep history based on past sleep history and/or the individual's schedule as maintained on a calendar, a combination of the last two, or alternatively assuming no sleep. In at least one embodiment, a projected sleep history is based on the average bedtime and the average wake-up time for the last x number of days (where x is any number between 1 and 15) is used for determining when future sleep will occur. In at least one embodiment, where the individual's schedule is accessible by the computing device, reviewing the individual's calendar to see if there are any time commitments that might interfere with sleep patterns between the current time and the future time. FIG. 8 illustrates an example cognitive gauge divided into three parts, which in this embodiment are analogous to blood-alcohol content levels in the U.S.

Turning now to FIG. 9, a sleep log is available for display and review by the user, showing a chronological listing 910 of the dates, times and duration of sleep intervals logged/entered by the user over time when the sleep schedule 920 is selected. The illustrated interface allows for entry of additional sleep periods via the "+" icon 930; and, in at least one embodiment, the "+" icon 930 also is used to add caffeine consumption (see FIG. 10) when the caffeine schedule 940 is being displayed in the illustrated interface.

FIG. 10 illustrates an embodiment in which a GUI allows the user of the system or digital application to enter in a caffeine dosing event by characterizing its source from a list of consumables 1010. Each consumable has an estimated caffeine dose associated with it in resident memory for input into the model.

FIG. 11 is an embodiment illustrating a GUI wherein the user's caffeine event log 940 is accessible and easily reviewable by the user. In the illustrated GUI, each caffeine event is listed by its date and time and approximate dose of caffeine.

Turning to FIG. 12, an example of a PVT test is shown as resident within the system. A user is asked to press the screen displaying a timer 1210. The user's reaction times are stored by the system for training the individual prediction mode and for assessing the current state of the user's cognitive performance/alertness.

In FIG. 13, a line graph 1310 of the model's predictions as trained on average group performance inputs 1305 is illustrated. The time of day is displayed on the x-axis and the reaction time (in milliseconds) is displayed on the y-axis. The individual user's mean reaction times are shown in the green dotted line 1320. The model's predicted alertness level based on the user's inputs and the group training, indicated as a function of reaction time, is shown in the solid yellow line 1330. The prediction is bounded both at upper and lower limits by the confidence interval as dashed-yellow lines 1340, 1350. The level of alertness/cognitive performance for the user is gauged as good, adequate or poor based on the reaction times using a "traffic light" color scale although other colors could be used. Actual and predicted reaction times in the lower, green range correlate to normal cognitive performance. Reaction times in the middle, yellow range correlate to degraded cognitive performance. Reaction times in the upper, red range correlate to cognitive performance that is severely impacted by sleep deprivation. Blue sections of the graphic correspond to sleep events 1360. An input are (drop-down menu) may be accessed to select the duration of the time window 1370 for the desired analysis, in the illustrated example, 3 days. A corresponding date range corresponds to the time window selected.

The model may also be trained using individual user inputs rather than group mean predictions. A user may easily select either model by selecting the appropriate model option in the GUI (see FIGS. 13 and 14) 1305/1407. Should the user select an individualized prediction based on previous, individual inputs, a graphic similar to the above will be displayed. In both cases, whether using group or individual predictions, a graphic may be generated for a date range 1580 that projects into the future as shown in FIG. 15. An indication of the current time may also be displayed, such as a white line as in this case.

Figure 19:
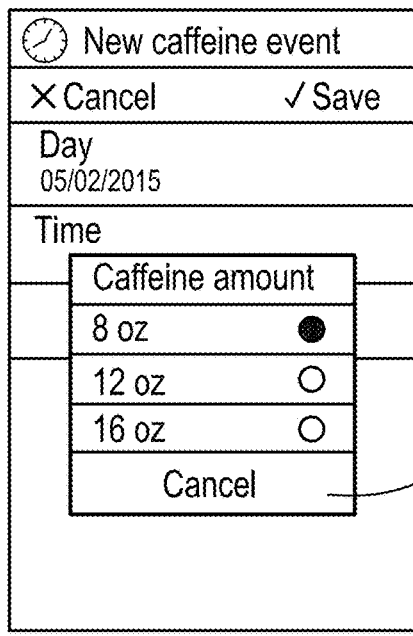
FIG. 19 illustrates a graphical user interface display relaying a user caffeine input interface.

Turning now to FIG. 16, a GUI screen is illustrated as presenting a user interface for inputting sleep events into the sleep log. In at least one embodiment, the user enters in a date using a calendar input 1710 as show in FIG. 17 and time 1810 as shown in FIG. 18 for the start and finish times of the sleep event. This information is stored in resident memory and used to model the predicted performance of the user based on group or individualized training inputs. Similarly, the user may update the caffeine event log by using an interface such as shown in FIG. 19 as an illustration of one embodiment of the invention. Here the user is allowed to select the size 1910 of the caffeinated beverage being consumed by the user. The size of the beverage corresponds to approximate caffeine doses that are stored and referenced in resident system memory.

Figure 20:
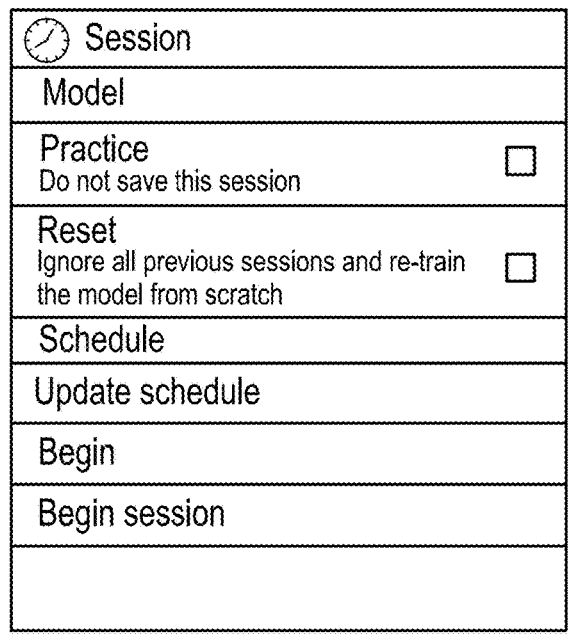
FIG. 20 illustrates a graphical user interface display relaying a model training session interface.

When training the system for individualized predictions, as user can access training sessions through a training session GUI portal similar to that shown in FIG. 20 for illustrative purposes. For example, the user may practice sessions to gain an understanding of how the system is trained for individualized predictions, thus helping to avoid modeling inaccuracies due to operator error. In at least one embodiment, the user is afforded the opportunity to reset the model to its default, untrained state by selecting the corresponding reset option. The interface also allows the user to update the session schedule and begin a training session.

Figure 21:
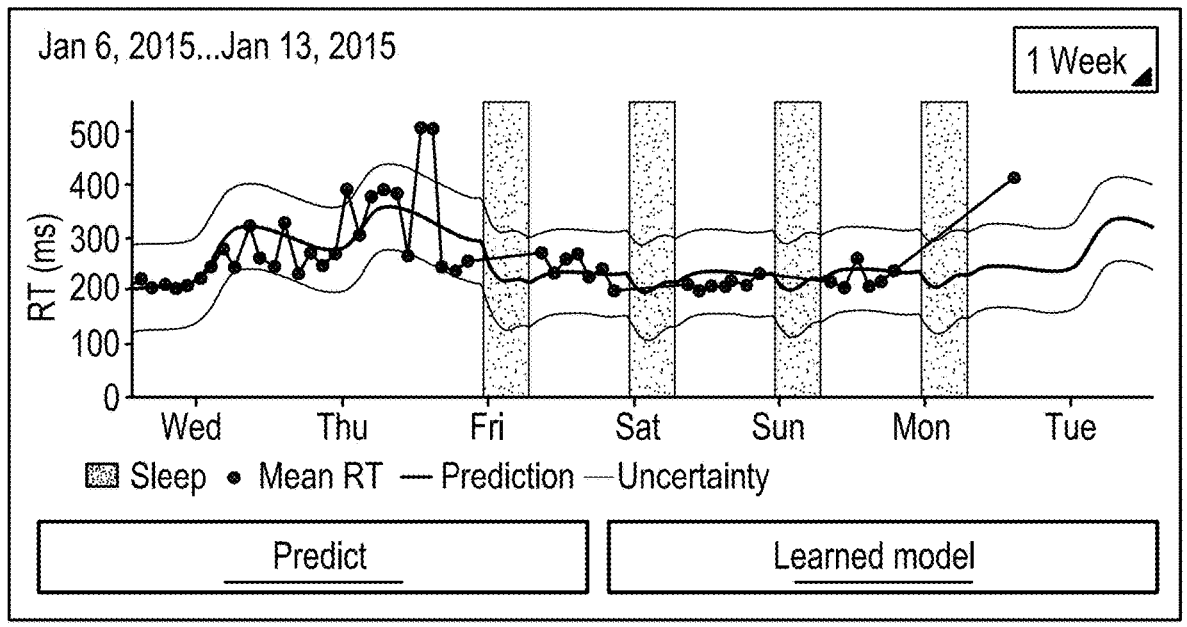
FIG. 21 illustrates a graphical user interface display relaying the results of trained model.
Figure 22:
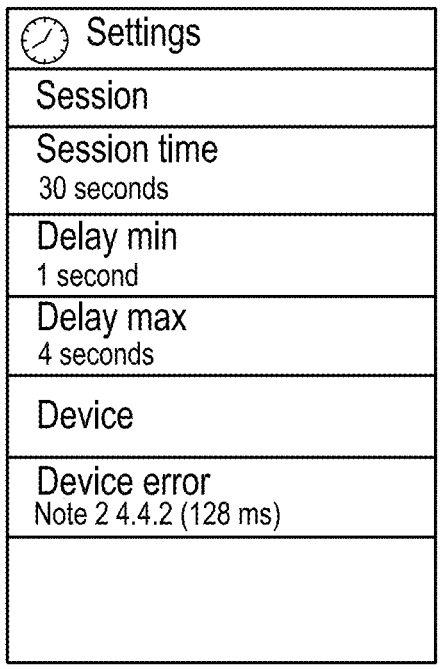
FIG. 22 illustrates a graphical user interface display relaying a model training session overview.
Figure 23:
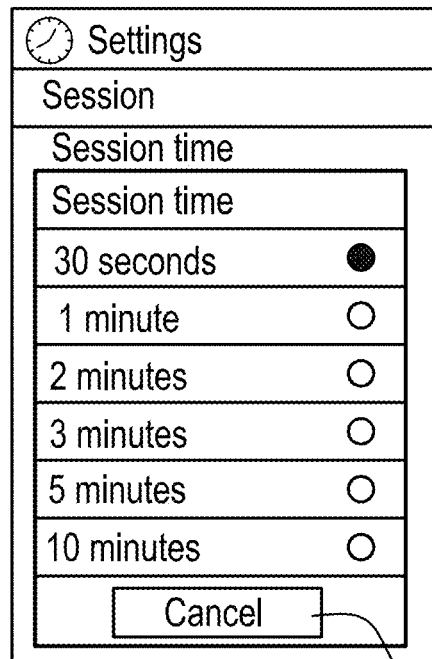
FIG. 23 illustrates a graphical user interface display relaying a model training session input interface.

By training a model, a user can use a "learned model" to predict individualized cognitive/alertness performance into the future, as for example, a day in advance after providing a week's worth of session training as shown in FIG. 21. The log of the training sessions may also be accessed through a separate GUI system interface as shown in FIG. 22. The duration of the session time may also be selected 2310 by the user through a GUI interface such as that shown in FIG. 23.

FIG. 25 illustrates a software interface input menus and output plots that appear upon login into the system in at least one embodiment. The illustrated interface allows for user inputs into the system that includes (1) sleep schedule (day and time of sleep start and sleep end) 2510 and (2) caffeine schedule (day, time, and dose of caffeine, which are selected using a drop-down menu) 2520, for the same time zone. In at least one embodiment, for each schedule, users may input up to 100 separate sleep periods and up to 400 separate caffeine consumption events (one event=timing+dosage entry). Each sleep/caffeine schedule can be saved using a unique schedule name (e.g., "Sleep Restriction+Caffeine" 2530). Sleep and caffeine inputs in at least one embodiment are entered manually via the web-browser interface or imported 2532, for example from a Microsoft Excel® compatible file using a predefined format. Alternatively, the computing device illustrated in FIGS. 5A and 5B or a body-worn data collection unit may provide sleep history information to the system.

For each sleep/caffeine schedule, the system generates performance predictions for three PVT statistics: number of lapses (lapse=response time≥500 ms), mean response time, and mean speed (i.e., mean reciprocal response time). Users choose which statistic to plot via the "Alertness Statistic" drop-down menu 2540. The sleep/caffeine input schedules and corresponding predicted outputs can be saved as an Excel® formatted file via the "Export Data" function button 2534; the displayed plots can be saved as an image file via the "Export Graph" function button 2536.

In at least one embodiment, there is a set of initial conditions and model assumptions. The model neurobehavioral performance predictions are initialized to 8 hours of sleep per night (23:00-07:00), and the system assumes that there is no sleep debt before day "0." From that point, user entries of 8 hours of sleep per day add no sleep debt (i.e., maintains daily performance at its initial level, plus/minus circadian variation). User entries of sleep durations <8 hours per day degrade performance, and sleep durations >8 hours per day improve performance. Consistent with the previously referenced "fading memory" concept, the more recent the sleep/wake period, the greater its influence on predicted performance.

The illustrated line graph 2550 shows how multiple schedules may be displayed at once ("sleep restriction+caffeine" 2552 and "new schedule" 2554). The line graph 2550 also shows when sleep 2556 is present in the sleep history. Similar to FIGS. 8 and 13-15, the line graph 2550 is divided into three vertical sections.

As discussed earlier, caffeine effects on performance are multiplicative, where the magnitude of change in performance due to caffeine is a function of the (1) size of the caffeine dose (in mg), (2) duration of time since the last caffeine event, and (3) time of day of the caffeine event.

FIG. 26 illustrates a further example of a system architecture according to at least one embodiment. In at least one implementation the system is hosted on an Apache Tomcat® web server that is accessible via a secure service over Hypertext Transfer Protocol Secure (https). The system uses a three-tier architecture composed of a backend database, a controller, and presentation tiers. The first tier includes an Oracle® database server that stores user account information to provide secure access to the system. The second (controller) tier provides access to the prediction engine and implements the functionality required to create and manage multiple predictions. The third (presentation) tier provides interactive plotting capabilities for multiple predictions with the ability to dynamically zoom on the x-axis of the plots as illustrated in FIG. 26. The illustrated and discussed controller and presentation tiers of this implementation were developed using Java™ Platform, Java™ Enterprise Edition 7, JavaServer Faces 2.2, and PrimeFaces 5.2 technologies. The graphical user interface in the presentation tier uses web standards supported by modern web browsers such as the Internet Explorer® browser, the Google Chrome browser, and the Mozilla Firefox browser, without any need for plugins.

Although the methods discussed in this disclosure are done without reference to particular flowcharts, it should be understood that the order of the steps shown to be varied from the order illustrated in other embodiments, that steps discussed as being separate can be combined (e.g., various displays and request for data can be combined into a single output screen), and that not all steps illustrated are necessarily required in all embodiments. Additionally in at least one embodiment where the implementation uses a processor, the processor executes code for the steps as such is an example of means for performing the discussed function.

While a specific embodiment of the invention will be shown and described in detail to illustrate the application of the principles of the invention, it will be understood that the invention may be embodied otherwise without departing from such principles.

What is claimed is:

1. A system adapted to be worn by a user for providing a cognitive level to the user where the cognitive level is representative of an ability for the user to perform cognitive functions, the system comprising:
 a user interface having a display and a receiving means for receiving input from the user;
 an accelerometer adapted to be worn by the user and configured to detect movement,
 at least one memory configured to store an alertness model and data associated with the user; and
 a processor in electrical communication with said user interface, said accelerometer, and said at least one memory; said processor configured to
  receive a signal from said accelerometer to monitor a level of activity of the user,
  convert the signal from said accelerometer into sleep-wake data representing whether the user is asleep or awake based on the level of activity,
  store the sleep-wake data obtained from the signal in said at least one memory,
  when caffeine consumption information is received from said receiving means, store the caffeine consumption information in said at least one memory as a caffeine consumption data,
  determine a cognitive level for the user with the alertness model based on the stored sleep-wake data and the stored caffeine consumption data,
  display the cognitive level on said display to the user,
  upon request, a predetermined schedule, when activity is detected or a combination of these, perform a response time test with said processor and said user interface by
   displaying a visual cue on said display,
   receiving a user response to the visual cue through said receiving means,
   calculating a response time, and
   repeating said displaying, receiving and calculating a plurality of times to determine a tested cognitive level;
  determine an offset between the model-determined cognitive level and the tested cognitive level;
  adjust at least one parameter weight in the alertness model based on the determined offset to individualize the alertness model for a sleep-loss phenotype of the user; and
  wherein the processor will initiate the response time test at least once every four hours of the user being awake during model individualization; and
 wherein the alertness model includes
  a homeostatic component having a sleep debt lower asymptote that varies based on a sleep debt for the user and a sleep debt upper asymptote, the homeostatic component increases exponentially with time awake and decreases exponentially with sleep time to a basal value, the homeostatic component uses the sleep-wake data;
  a circadian component with an adjustable circadian amplitude; and
  a caffeine component that provides a multiplicative impact on a sum of the homeostatic component and the circadian component, the caffeine component uses caffeine consumption data present in said at least one memory at distinct dosage times to provide an exponential decay of the caffeine consumption over time, the caffeine component is equal to 1 prior to a first time of distinct caffeine consumption data, and
 the user is able to act on the displayed cognitive level to address any fatigue and/or impairment as represented by the displayed cognitive level by adjusting a sleep schedule and/or caffeine consumption.

2. The system according to claim 1, wherein said processor uses a Bayesian model and a plurality of offsets to improve the alertness model fit to the user.

3. A system comprising:
 the system adapted to be worn by the user according to claim 1; and
 a server, and
 wherein said processor transmits the at least one alertness model parameter weight to said server;
 said server capable of electrical communication with said processor, said server configured to
  receive at least one alertness model parameter weight from said processor,
  store the received at least one alertness model parameter weight in a database associated with the user of said worn system that sent the at least one alertness model parameter weight, and
  provide a planning interface to model different timing and amounts of sleep and caffeine consumption to provide a forecast for future cognitive levels or a regression for past cognitive levels for the user associated with the at least one alertness model parameter weight.

4. The system according to claim 3, wherein said server is configured to receive projected sleep time and/or caffeine consumption for the user and project a future cognitive level using the projected sleep time and/or caffeine consumption for the user.

5. The system according to claim 3, further comprising a communications module in communication with said processor, said communications module configured to communicate with said server for further processing of the data stored in said at least one memory.

6. The system according to claim 1, wherein said processor displays an alertness gauge on said display to show the user a graphical representation of their current cognitive level relative to at least two benchmark cognitive levels.

7. The system according to claim 1, wherein said alertness model includes $P_c(t) = (S(t) + \kappa C(t)) * g_{PD}(t,c)$ where S(t) represents the homeostatic component, C(t) represents the circadian component, and $g_{PD}(t,c)$ represents the caffeine component and where $$C(t) = \sum_{i=1}^{5} a_i \sin\left[i\frac{2\pi}{\tau}(t + \phi)\right]$$

where i represents harmonics, $a_1=0.97$, $a_2=0.22$, $a_3=0.07$, $a_4=0.03$, and $a_5=0.001$, $\tau$ denotes a period of a circadian oscillator, $\kappa$ represents a circadian amplitude, and $\Phi$ denotes a circadian phase, and $$S(t) = \begin{cases} U - (U - S_0)\exp(-t/\tau_w) & \text{during wakefulness} \\ -2U + (2U + S_0)\exp(-t/\tau_s) + & \text{during sleep} \\ (2U + L_0)[\tau_{LA}/(\tau_{LA} - \tau_s)] \\ [\exp(-t/\tau_{LA}) - \exp(-t/\tau_s)] \end{cases}$$

where U and L denote the sleep debt upper asymptote and the sleep debt lower asymptote of process S, respectively, $\tau_w$ and $\tau_s$ denote time constants, and $\tau_{LA}$ denotes the time constant of an exponential decay of an effect of sleep history on cognitive performance, where $L(t) =$ $$\begin{cases} \max[U - (U - L_0)\exp(-t/\tau_{LA}), -0.11U] & \text{during wakefulness} \\ \max[-2U + (2U + L_0)\exp(-t/\tau_{LA}), -0.11U] & \text{during sleep} \end{cases}$$

where $$g_{PD}(t, c) = \left[1 + M_c \frac{k_a}{k_a - k_c}\{\exp[-k_c(t - t_0)] - \exp[-k_a(t - t_0)]\}\right]^{-1}$$

for $t \geq t0$ $M_c = M_0 \cdot c$ and $k_c = k_0 \exp(-z \cdot c)$ where $M_c$ and $k_c$ denote an amplitude factor and an elimination rate for a caffeine dose c administered at time $t_0$, $M_0$, $k_0$, z, and $k_a$ denote an amplitude slope, a basal elimination rate, a decay constant, and an absorption rate.

8. The system according to claim 1, wherein said alertness model includes $P_c(t) = (S(t) + \kappa C(t)) * g_{PD}(t,c)$ where S(t) represents the homeostatic component, C(t) represents the circadian component, and $g_{PD}(t,c)$ represents the caffeine component and where $$C(t) = \sum_{i=1}^{5} a_i \sin\left[i\frac{2\pi}{\tau}(t + \phi)\right]$$

where i represents harmonics, $a_1=0.97$, $a_2=0.22$, $a_3=0.07$, $a_4=0.03$, and $a_5=0.001$, $\tau$ denotes a period of a circadian oscillator, $\kappa$ represents a circadian amplitude, and $\Phi$ denotes a circadian phase, and $$S(t) = \begin{cases} U - (U - S_0)\exp(-t/\tau_w) & \text{during wakefulness} \\ -2U + (2U + S_0)\exp(-t/\tau_s) + & \text{during sleep} \\ (2U + L_0)[\tau_{LA}/(\tau_{LA} - \tau_s)] \\ [\exp(-t/\tau_{LA}) - \exp(-t/\tau_s)] \end{cases}$$

where U and L denote the sleep debt upper asymptote and the sleep debt lower asymptote of process S, respectively, $\tau_w$ and $\tau_s$ denote the time constants, and $\tau_{LA}$ denotes the time constant of an exponential decay of an effect of sleep history on cognitive performance, where $L(t) =$ $$\begin{cases} \max[U - (U - L_0)\exp(-t/\tau_{LA}), -0.11U] & \text{during wakefulness} \\ \max[-2U + (2U + L_0)\exp(-t/\tau_{LA}), -0.11U] & \text{during sleep} \end{cases}$$

where $$g_{PD}(t, c) = \left[1 + M_c \frac{k_a}{k_a - k_c}\{\exp[-k_c(t - t_0)] - \exp[-k_a(t - t_0)]\}\right]^{-1}$$

for $t \geq t0$ $M_c = M_0 \cdot c$ and $k_c = k_0 \exp(-z \cdot c)$ where $M_c$ and $k_c$ denote an amplitude factor and an elimination rate for a caffeine dose c administered at time $t_0$, $M_0$, $k_0$, z, and $k_a$ denote an amplitude slope, a basal elimination rate, a decay constant, and an absorption rate; and wherein parameter weights for $\tau_w$, $\tau_s$, $\varphi$, $\kappa$, and $\tau_{LA}$ are adjustable.

9. The system according to claim 1, wherein said receiving means is configured to receive a future time from the user, and said processor configured to project the cognitive level at the future time where the user is projected to be awake between now and the future time and where the user is projected as maintaining recent sleep patterns between now and the future time where recent sleep patterns are based on stored activity data.

10. A system comprising:

a plurality of computing devices where each computing device is assigned to a user, each of said computing devices having a user interface having a display and receiving means for receiving input from the user;

an accelerometer adapted to be worn by the user and configured to detect movement;

at least one memory configured to store an alertness model and data associated with the user;

a communications module; and a processor in electrical communication with said user interface, said accelerometer, said communications module, and said at least one memory; said processor configured to receive a signal from said accelerometer to monitor a level of activity of the user, convert the signal from said accelerometer into sleep-wake data representing whether the user is asleep or awake based on the level of activity, store the sleep-wake data obtained from the signal in said at least one memory, when caffeine consumption information is received from said receiving means, store the caffeine consumption information in said at least one memory as caffeine consumption data, determine a cognitive level for the user with the alertness model based on the stored sleep-wake data and the stored caffeine consumption data, and display the cognitive level on said display, upon request, a predetermined schedule, when activity is detected or a combination of these, perform a response time test with said processor and said user interface by displaying a visual cue on said display, receiving a user response to the visual cue through said receiving means, calculating a response time, and repeating said displaying, receiving and calculating a plurality of times to determine a tested cognitive level;

determine an offset between the model-determined cognitive level and the tested cognitive level;

adjust at least one parameter weight in the alertness model based on the determined offset to individualize the alertness model for a sleep-loss phenotype of the user; and wherein the processor will initiate the response time test at least once every four hours of the user being awake during model individualization; and a server capable of communication with each of said plurality of computing devices, said server configured to receive alertness model weights from said processors through said respective communications modules, store received alertness model weights in a database associated with the user associated with said computing device that sent the alertness model weights, and provide a planning interface to model different timing and amounts of sleep and caffeine consumption to provide a forecast for future cognitive levels or a regression for past cognitive levels for the user associated with the alertness model weights; and wherein the alertness model includes a homeostatic component having a sleep debt lower asymptote that varies based on a sleep debt for the user and a sleep debt upper asymptote, the homeostatic component increases exponentially with time awake and decreases exponentially with sleep time to a basal value, the homeostatic component uses the sleep-wake data;

a circadian component with an adjustable circadian amplitude; and a caffeine component that provides a multiplicative impact on a sum of the homeostatic component and the circadian component, the caffeine component uses caffeine consumption data present in said at least one memory at distinct dosage times to provide an exponential decay of the caffeine consumption over time, the caffeine component is equal to 1 prior to a first time of distinct caffeine consumption data is present in said at least one memory, and the user is able to act on the displayed cognitive level to address any fatigue and/or impairment as represented by the displayed cognitive level.

11. The system according to claim 10, wherein said server is configured to receive projected sleep time and/or caffeine consumption for each user and project a future cognitive level using the projected sleep time and/or caffeine consumption for each user.

12. The system according to claim 10, wherein said processor uses a model selected from the group consisting of one of a Bayesian model and a recursive model and a plurality of offsets to improve the alertness model fit to each user.

13. A method for determining a cognitive state of an individual using a computing device having a processor, a memory, an accelerometer, a display, and a receiving means for receiving input from the individual about the individual including caffeine consumption, the method comprising:

receiving a signal from the accelerometer configured to monitor a level of activity of the individual, converting the signal from said accelerometer into sleep-wake data representing whether the individual is asleep or awake based on the level of activity, storing the sleep-wake data obtained from the signal in the memory, storing a caffeine consumption information in the memory as caffeine consumption data as caffeine consumption information is received from the receiving means, determining a cognitive level for the individual with an alertness model based on the stored data including the sleep-wake data and caffeine consumption data, and displaying the cognitive level on the display; and wherein the alertness model includes a homeostatic component having a sleep debt lower asymptote that varies based on a sleep debt for the individual and a sleep debt upper asymptote, the homeostatic component increases exponentially with time awake and decreases exponentially with sleep time to a basal value, the homeostatic component uses the sleep-wake data;

a circadian component with an adjustable circadian amplitude; and a caffeine component that provides a multiplicative impact on a sum of the homeostatic component and the circadian component, the caffeine component uses caffeine consumption data present in the memory at distinct dosage times to provide an exponential decay of the caffeine consumption over time, the caffeine component is equal to 1 prior to a first time of distinct caffeine consumption data is present in the memory, and a user and/or the individual acts on the displayed cognitive level to address any fatigue and/or impairment of the individual as represented by the displayed cognitive level.

14. The method according to claim 13, further comprising:

performing a response time test with the processor at least every four hours the individual is awake during model individualization, the display and the receiving means, where preforming the response time test includes displaying a visual cue on the display, receiving a response from the individual to the visual cue through the receiving means, calculating a response time, and repeating the displaying, receiving and calculating a plurality of times to determine a tested cognitive level;

determining an offset between the model-determined cognitive level and the tested cognitive level;

adjusting at least one parameter weight in the alertness model based on the determined offset to individualize the alertness model for a sleep-loss phenotype of the individual.

15. The method according to claim 14, wherein displaying the cognitive level includes
   presenting at least a current cognitive level and past cognitive levels as determined by the alertness model as a cognitive line between two uncertainty lines over a color gradient representing three levels of impairment for the individual, and
   displaying the tested cognitive levels over the cognitive line;
the at least one adjustable parameter weight in the alertness model includes the sleep debt upper asymptote in the homeostatic component and the adjustable circadian amplitude and a circadian phase in the circadian component while not adjusting any time constants;
the visual cue displayed during the response time is a numerical representation of response time starting from when the visual cue is displayed running until the individual responds;
the computing device is worn by the individual; and
the individual may act on the displayed information by sleeping or consuming caffeine to reduce the level of impairment.

16. The method according to claim 13, further comprising providing a future cognitive level by using a sleep history provided by the user or the individual, a projected sleep history based on recent sleeping patterns such that an average bedtime and an average wake time are used to determine when sleep will occur, and/or assumption that no sleep will occur between a current time and a time for the future cognitive level.

17. The method according to claim 13, further comprising displaying a graphical user interface upon a caffeine request from the individual, where the graphical user interface is configured to receive entry of a type of caffeine consumed and the amount of caffeine consumed.

* * * * *